United States Patent
Yakymovych et al.

(10) Patent No.: US 11,478,484 B2
(45) Date of Patent: Oct. 25, 2022

(54) METHOD FOR PREPARING A LIPOSOMAL COMPOSITION COMPRISING LATANOPROST, AND THE PHARMACOLOGICALLY ACTIVE LIPOSOMAL COMPOSITION FOR OPHTHALMOTHERAPY PREPARED BY THIS METHOD

(71) Applicant: CONSORTIUM "UKRINDUSTRY", Kyiv (UA)

(72) Inventors: Pylypenko Oleksandr Yakymovych, Kyiv (UA); Grygorieva Ganna Savivna, Kyiv (UA); Krasnopolskyi Yurii Myhaylovych, Kharkov (UA); Konahovych Nataliia Philimonivna, Vasylkiv (UA); Myheytseva iryna Mykolaivna, Odesa (UA); Pasiechnikova Nataliia Volodymyrivna, Kyiv (UA); Prokhorov Vitalii Valentynovych, Kharkov (UA)

(73) Assignee: Consortium "Ukrindustry", Kyiv (UA)

( * ) Notice: Subject to any disclaimer, the term of this patent is extended or adjusted under 35 U.S.C. 154(b) by 0 days.

(21) Appl. No.: 17/375,814

(22) Filed: Jul. 14, 2021

(65) Prior Publication Data
US 2022/0305028 A1 Sep. 29, 2022

(30) Foreign Application Priority Data
Mar. 26, 2021 (UA) ................................ a 2021 01614

(51) Int. Cl.
| | |
|---|---|
| *A61K 31/5575* | (2006.01) |
| *A61K 9/127* | (2006.01) |
| *A61K 9/00* | (2006.01) |
| *A61K 47/28* | (2006.01) |
| *A61P 27/06* | (2006.01) |
| *A61K 47/24* | (2006.01) |

(52) U.S. Cl.
CPC ........ *A61K 31/5575* (2013.01); *A61K 9/0019* (2013.01); *A61K 9/0048* (2013.01); *A61K 9/127* (2013.01); *A61K 9/1277* (2013.01); *A61K 47/24* (2013.01); *A61K 47/28* (2013.01); *A61P 27/06* (2018.01)

(58) Field of Classification Search
CPC .. A61K 31/5575; A61K 9/127; A61K 9/1277; A61K 9/0048; A61P 27/06
See application file for complete search history.

(56) References Cited

U.S. PATENT DOCUMENTS

2013/0216606 A1* 8/2013 Venkatraman ......... A61K 9/127
514/530
2019/0211033 A1* 7/2019 Wiles ................... C07D 401/14

FOREIGN PATENT DOCUMENTS

| SG | 187770 A1 | 3/2013 |
|---|---|---|
| WO | WO-2012/021107 A2 | 2/2012 |

OTHER PUBLICATIONS

Resnikoff, S. et al., "Global data on visual impairment in the year 2002," *Bulletin of the World Health Organization*, Nov. 2004, pp. 1-9.
Quigley, H. A. et al., "The number of people with glaucoma worldwide in 2010 and 2020," *Br J Opthalmol.*, 2006, 90:262-267.
Zavgorodnyaya, N.G. et al., "Primary glaucoma. A new look at an old problem," 2010, pp. 1-192, along with its English abstract.
Hoyng, P.F.J. et al., "Pharmacological therapy for glaucoma: a review," *Drugs*, 2000, 59(3):411-434, abstract only.

(Continued)

*Primary Examiner* — Michael B. Pallay
(74) *Attorney, Agent, or Firm* — Saliwanchik, Lloyd & Eisenschenk

(57) ABSTRACT

A group of inventions relates to pharmaceutics and refers to a method for preparing a liposomal composition and a pharmacologically active liposomal composition for ophthalmotherapy prepared by this method. The method is implemented by creating a mixture of solutions of latanoprost, egg phosphatidylcholine and cholesterol in organic solvents, vacuum drying thereof, emulsifying in an aqueous medium, and dispersing an emulsion under pressure. According to the invention, a solution of dipalmytoyl phosphatidylglycerol is introduced into the mixture of solutions, wherein latanoprost, egg phosphatidylcholine, and cholesterol are dissolved in ethyl alcohol, while dipalmytoyl phosphatidylglycerol is dissolved in a mixture of ethyl alcohol and chloroform. The emulsifying of the dried mixture is conducted by a lactose solution in a pH 7.1 buffer, while the dispersing of the emulsion is conducted at a stepwise pressure increase from 300 to 800 at followed by a sterilizing filtration and a freeze drying.
The composition prepared by this method is a frozen-dried powder and a formulation thereof comprises:
Latanoprost 1,
Egg phosphatidylcholine 20.0-30.0,
Dipalmytoyl phosphatidylglycerol 0.6-0.75,
Cholesterol 0.5-0.9,
Lactose 40.0-60.0,
Water residue the remainder.
The pharmacologically active liposomal composition has a prolonged antihypertensive and neuroprotective action in case of ocular hypertension and glaucoma, and it is suitable for preparation a solution for an instillation use and/or injectable subconjunctival administration.

2 ind.cls., 2 d.cls.

4 Claims, 7 Drawing Sheets

(56) References Cited

OTHER PUBLICATIONS

Andrés-Guerrero, V. et al., "Comparison of the In Vitro Tolerance and In Vivo Efficacy of Traditional Timolol Maleate Eye Drops versus new Formulations with Bioadhesive Polymers," *Investigative Ophthalmology & Visual Science*, May 2011, 52(6):3548-3556, The Association for Research in Vision and Ophthamology, Inc.

Lindén, C. et al., "The effect on intraocular pressure of latanoprost once or four times daily," *Br J Ophthalmol*, 2001, 85:1163-1166.

"Liposome Advances Progress in Drug and Vaccine Delivery," *International Liposome Society and Liposome Research Days Combined Conference*, Sep. 16-18, 2017, pp. 1-9.

Ako-Adounvo, A. et al., "Recent Patents on Ophthalmic Nanoformulations and Therapeutic Implications," *Recent Pat Drug Deliv Formul.*, 2014, 8(3):193-201, Bentham Science Publishers.

Cheng, Y. et al., "Sustained delivery of latanoprost by thermosensitive chitosan-gelatin-based hydrogel for controlling ocular hypertension," *Acta Biomaterialia*, Oct. 2014, 10(10):4360-4366, abstract only.

Fathalla, D. et al. "Latanoprost niosomes as a sustained release ocular delivery system for the management of glaucoma," Drug Development and Industrial Pharmacy, 2020, 46(5):1-4, Taylor & Francis Online.

Grigoriev, G.S. et al. "Liposomes perse: pharmacotherapeutic status," Pharmacology and drug toxicology, 2020, 14(4):264-271, along with its English translation.

Natarajan, J. V. et al., "Sustained Release of an Anti-Glaucoma Drug: Demonstration of Efficacy of a Liposomal Formulation in the Rabbit Eye," Plos One, 2011, 6(9): e24513 (pp. 1-10).

Wong, T. T. et al., "Nanomedicine for glaucoma: sustained release latanoprost offers a new therapeutic option with substantial benefits over eyedrops," *Drug Delivery and Translational Research*, Mar. 31, 2014, 4:303-309, Springer Nature, abstract only.

Natarajan, J. V. et al., "Nanomedicine for glaucoma: liposomes provide sustained release of latanoprost in the eye," International Journal of Nanomedicine, Jan. 4, 2012, 7:123-131, Dove Medical Press Ltd.

Franzé, S. et al., "Lyophilization of Liposomal Formulations: Still Necessary, Still Challenging," *Pharmaceutics*, Aug. 28, 2018, 10(139):1-23, MDPI.

Gregoriadis, G. "Interactions of Liposomes with the Biological Milieu," Liposome Technology, 1993, 3(2):1-432, CRC Press, https://books.google.com.ua/books?hl=uk&lr=&id=1qQzNrNaFRYC&oi=fnd&pg=PP22&dq=G.+Gregoriadis+(ed.),+Liposome+Technology,&ots=AH9s15X8k-&sig=ZnZHWjbi1HS8A5svQICSoacE8NY&redir_esc=y#v=onepage&q=G.%20Gregoriadis%20(ed.)%2C%20Liposome%20Technology%2C&f=false.

Wong, T. T. et al., "Safety and Efficacy of Liposomal Latanoprost in Ocular Hypertension," Clinical Trials, 2013, pp. 1-5, Singapore Eye Research Institute.

Strasbourg, "European Convention for the Protection of Vertebrate Animals used for Experimental and Other Scientific Purposes," European Treaty Series, Mar. 18, 1986, 123:1-11, Council of Europe.

Kim, H. G. et al., "Experimental chronic ocular hypertension by anterior chamber injection of 0.3% carbomer solution in the rat," Clinical & Experimental Ophthalmology, 2013, 41(4):404-412.

Xu, Y. et al., "A study of experimental carbomer glaucoma and other experimental glaucoma in rabbits," Zhonghua Yan Ke Za Zhi (Chinese Journal of Ophthalmology), Mar. 2002, 38(3):172-175.

Egorov, E. A. et al., "Neuroprotection in Glaucoma: Current Opportunities and Prospects," Clinical Ophthamology, 2014, 14(2):108-112, along with its English translation.

Yoles, E. et al., "Elevation of Intraocular Glutamate Levels in Rats With Partial Lesion of the Optic Nerve," *Arch Ophthalmol.*, 1998, 116:906-910, American Medical Association.

* cited by examiner

METHOD FOR PREPARING A LIPOSOMAL COMPOSITION COMPRISING LATANOPROST, AND THE PHARMACOLOGICALLY ACTIVE LIPOSOMAL COMPOSITION FOR OPHTHALMOTHERAPY PREPARED BY THIS METHOD

CROSS-REFERENCE TO RELATED APPLICATION

This application claims priority to Ukrainian Application No. a 2021 01614, filed Mar. 26, 2021, which is hereby incorporated by reference in its entirety.

The invention refers to pharmaceutics and relates to a method for preparing a pharmacologically active liposomal composition comprising latanoprost, and to the liposomal composition prepared by this method that may be used as an agent for pharmacotherapy of an ocular hypertension and glaucoma in ophthalmology.

An increased intraocular pressure (IOP) is a serious ophthalmologic pathology that, in case of chronicity and in absence of an adequate treatment, leads to an optic nerve disorder and to formation of glaucoma. Glaucoma is a chronic optic neuropathy found in more than 90 millions of patients worldwide that is attributed to main causes of an irreversible blindness [1,2].

A counteraction against a negative trend and a fatal consequence of the optic neuropathy requires efforts on reducing the pathological IOP in an effective way. Despite on certain achievements of a laser and a drainage surgery, a priority way to resolve this important problem is to create and to use pharmacotherapeutic agents [3,4]. According to experimental and clinical data, carboxy anhydrase inhibitors, adrenergic antagonists, and parasympathomimetics are considered amongst physiologically active IOP-reducing substances, but in terms of criteria of the highest efficiency and harmlessness, β-adrenergic blocking agents and prostaglandin analogues are attributed to first-line drugs. The latter predominate the β-adrenergic blocking agents in terms of an influence onto trabecular and uveoscleral outflow, and thus, in terms of the IOP reduction effect [5].

An exemplary translation of use of prostaglandines in ophthalmology is mostly related to latanoprost (LP) being a synthetic phenyl-substituted F2a prostaglandin analogue that is a pro-drug that forms an active acidic form of the LP due to a hydrolysis of a primary ether form [6].

Specifically, the LP is selected as active pharmaceutical ingredient of the known drug Xalatan and its numerous generics (Lanotan, Latoprost, Monoprost, Akistan), which are proposed exclusively in form of an aqueous solution for ophthalmic drops. Nevertheless, an antihypertensive action for these agents regarding the TOP is accompanied by undesired factors. These include a short duration of the effect due to a low penetration of the latanoprost from the drops through a corneal epithelium (not more than 5% of the administered amount), thereby causing a need in daily repetitive instillations with the corresponding low patient compliance and disturbance of a treatment protocol, as well as adverse ophthalmic reactions (iris pigmentation, excitation and enhancement of inflammatory events in an anterior chamber of the eye) and an untargeted penetration of a portion of the administered latanoprost to a systemic blood circulation [7].

An effort to achieve a prolongation of the latanoprost effect with a simultaneous optimization of a benefit/risk profile and compliance has actualized a demand for methods for preparing products thereof, which are suitable for use, except for the dripping ones, in distinctive drug formulations according to the modern pharmacy paradigm "Drug delivery system" [8,9].

Preparation of systems for delivery of latanoprost in the gel form based on a thermally sensitive composition chitosan/gelatine/glycerophosphate [10] or a surfactant [11] has been described. Products of implementation of these methods upon a single administration prolong the TOP control only up to 3-8 days and do not meet the requirements of the ophthalmic safety (osmolality, transparency etc.).

As a priority way for preparing the LP agents, which are able to combine the prolonged pharmacotherapeutic regulation of the TOP and the optimal harmlessness with different ophthalmic delivery methods, creation of its composition on a liposomal phospholipid platform is considered. Feasibility of this approach is associated with a physiological parentage and a pharmacopoeial validity of liposomes, as well as with a positive experience of preparing and clinical worldwide use of liposomal drugs of a various specificity [12,13].

Patent materials and scientific data comprising descriptions of processes for preparing and pharmacological properties of liposomal compositions of latanoprost are known [14-20].

It should be noted that the patent history of this topic has a permanent development with duplication of subject matters and content of materials: the non-published application U.S. 61/372,962 dated Aug. 12, 2010 and the international application filed on the basis thereof PCT/SG 2011/000281 published under the number WO 2012/021107 A2 [14], which in turn was a basis for creation of two applications—US 2013/0216606 A1[15] (the corresponding patent U.S. Ser. No. 10/272,040 B2 dated Apr. 30, 2019) and SG187770 A1[16] (due to cancellation of the Singapore Intellectual Property Office, only a history of this application is known).

Therewith, scientific publications [17-20] regarding the preparation and ophthalmologic specificity of liposomal compositions of latanoprost, almost completely or with certain variations and cross-references, propose information that has been already made publicly available during the development of the patent history [14-16].

In view of said circumstances, only a simultaneous analysis of processing of the known methods and validity of the prepared products is expedient.

Hereafter, for the sake of convenience, there are reference designations of the key compounds mentioned in relation to the methods for preparing the liposomal latanoprost, as well as in the description of the claimed method and composition and in the prototype.

| Rational names of the compounds used | Reference designation |
| --- | --- |
| Latanoprost | LP |
| Phosphatidylcholine | PC |
| Egg phosphatidylcholine | ePC |
| Palmytoyl oleyl phosphatidylcholine | POPC |
| Dipalmytoyl phosphatidylglycerol | DPPG |
| Dipalmytoyl phosphatidylcholine | DPPC |
| Cholesterol | CHOL |

Preparation of the liposomal composition of LP based on ePC or POPC, or DPPC has been described [14-20].

According to [14,17], ePC or POPC is dissolved at a room temperature in a pH 6.7 phosphate buffer under shaking and extruded through a polycarbonate membrane to produce an emulsion that is used to wash out a film, which is dried from the LP solution in ethyl alcohol in a round flask at 50° C., until fatty drops are disappeared from the flask walls. In sterile conditions, the emulsion is filtered through a 200 nm membrane and the produced liquid product is stored at 4° C. until conduction of the analysis. The same method with certain variations as to the ratio LP:ePC, terms of dissolution of the ePC, and the product storage conditions (−20° C.), is described in [18]. A low validity of this method due to a subjectivity of control of the phospholipid dissolution stages in the buffer (lipids are not dissolved in aqueous medium) and washing out the LP film ("until fatty drops are disappeared from the flask walls") is obvious.

In [14,15,19], it is proposed to prepare a liposomal composition of LP with ePC or POPC by dissolving the phospholipid in a mixture chloroform:methanol, LP—in acetonitrile, after these solutions are combined, solvents are removed at 40° C. on a rotary evaporator until a film is produced that is washed out with a pH 5.5 phosphate buffer, performing extrusion through 200 nm/80 nm polycarbonate membranes, under aseptic conditions filtering through a 200 nm membrane and storing the produced liquid product at 4° C. An average size of the produced liposomes is from 90 to 120 nm. However, it should be noted that the preparation of the liposomal composition in the pH 5.5 phosphate buffer [14,19] does not meet the physiological conditions, as well as it does not facilitate a hydrolytic conversion of the prostaglandin F2a into the active form of LP.

A method for preparing the liposomal composition of LP with DPPC [20] that is synonymous [14,19] in terms of the processing and the product description is described, the method comprises an additional operation of ultrasound treatment of the LP film washouts to the pH 5.5 buffer prior to the extrusion conduction. However, such operation facilitates oxidation and destruction of the phospholipid and LP under exposure to US, as well as technically overburdens the method and makes its scaling impossible a priori.

An interrelation and a compilativity of the information in the considered sources [14-20] regarding the preparation of liposomes with LP impose a necessary conduction of a generalized evaluation of the produced products in terms of their quality and compliance for ophthalmology.

Liposomal compositions of LP based on ePC or POPC, or DPPC, or ePC+CHOL [14-20] are known, which are liquid-phase systems comprising liposomes having a size of from 80 to 120 nm in the pH 5.5 or pH 6.7 buffer medium. A gradual in vitro release of the incorporated LP is described for these products, which may define a prolonged influence onto the IOP in vivo for up to 90 days upon a single subconjunctival administration.

An ambiguous factor for such liposomal compositions of LP in the aqueous medium is a disputable stability during storage under the proposed conditions. Accordingly, no measures for protection of the product against a temperature stress are proposed for the storage at the temperature of −20° C. [17,18]. In case of absence thereof, as it is known [21,22], an irreversible destruction of the phospholipid membrane of the liposomes will take place. The mentioned information casts a doubt on the stability of the pharmaceutical quality of the known liquid-phase liposomal compositions of LP during storage.

The evidence of the pharmaceutical quality of the known liposomal compositions of LP is negatively affected by the used methodical conditions of evaluation of their ophthalmologic action.

Accordingly, in the known sources [14-20] the level and duration of the TOP reduction have been exclusively evaluated on normotensive rabbits without ocular hypertension (the physiological TOP norm for nonhuman primates used in one experiment is not known at all). In fact, for the known liposomal LP products, a hypotensive action regarding healthy animals has been described, while its level does not correlate with an antihypertensive effect in case of the ocular hypertension formed pathophysiologically.

Although the antiglaucomic effect of the known liposomal products of LP is proclaimed insistently [14-20], the antiglaucomic activity is paradoxically declared only for healthy animals, while an influence onto signs of the optic neuropathy is not confirmed. The pharmacological quality of the ePC-based liposomal composition of LP for the glaucoma is not proven in the ongoing clinical study [18]: contrary to the standards of the "Good Clinical Practice" GCP, only 6 patients were enrolled that made impossible to evaluate the data correctly; the patients were administered with an experimental sample of the composition that was received by a non-validated method and stored at the temperature −20° C. (in absence of a cryoprotector) that destroys the product's identity and stability. It is telling that the reliability of the results of this study has not been confirmed by the USA state regulatory authority [23]. Therefore, for said methods of preparing the liposomal LP composition, the pharmaceutical standardization of the products has not been proven correctly and the pharmacological quality as to regulation of the increased TOP and antiglaucomic effect has not been disclosed.

An array of information regarding preparation and pharmacological properties of the liposomal products of LP is comprised in the application US 2013/0216606 A1 [15] (patent U.S. Ser. No. 10/272,040 B2 dated Apr. 30, 2019) with a certain duplication of the data made publicly available in the sources [14, 16-20] during the development of the patent history and discussed above.

The source [15] declares a possibility of using a family of phosphatidylcholines to create liposomal agents for the ophthalmic transport of prostaglandines. Nevertheless, expansion of a universal method for creating liposomes with LP to the entire family of phosphatidylcholines is not disclosed, since preparation of liposomes is given only with LP and only based on ePC or DPPC according to the methods, which are close to the ones proposed in [17,18]. Therewith, the preparation processing is differ even for the alternative of these two phosphatidylcholines (US treatment of the LP film washouts in the buffer for the DPPC only, different ratios LP:lipid etc.).

The source [15] also declares introduction of a combination of phosphatidylcholines into the liposomes with LP, although a method for preparing liposomes with LP on the combined lipid platform has not been described, and a possible influence of the lipid combination onto the quality of the product is not expected.

The source [15] also proposes combining the phospholipid of the liposomal LP composition with additional components, among which sphingolipid or sterol lipid, or polyketide lipid, or stearyl amine, or cholesterol (taken alone) are mentioned, however, an algorithm for their introduction when implementing the method is not disclosed. In the only one specific case of combining the ePC with cholesterol or DPPC with stearyl amine, only a quantity of additives is mentioned without disclosing their influence onto the quality of the target product.

A liposomal ePC-based composition of LP is known, the composition comprises CHOL and is prepared by the method described in [15]. This method and the product of implementation thereof have been selected as a prototype of the claimed subject matter being a method for preparing a liposomal composition comprising LP and a liposomal composition prepared by this method, as its analogue with generalized features, namely: an essence and a sequence of certain operations of the method implementation, a liposomal organization of the created composition comprising LP, and a nature of certain components in the formulation thereof.

According to the prototype [15], the method for preparing the liposomal composition of LP comprises creation of a mixture of separate solvents, LP—in acetonitrile, ePC and CHOL—in a mixture of chloroform and methyl alcohol (2:1 by volume) in line with mass ratios of ePC:LP being 1:0.086 (molar ratio is 1:0.154) and of ePC+LP:CHOL being 1:0.10-0.40, vacuum drying thereof to produce a thin film to which a pH 5.5 phosphate buffer solution is added, and extruding the produced system on the Northvern Lipids extruder through polycarbonate filters having a pore diameter of 0.2/0.08 μm during successive cycles until an ultimate distribution of the sizes of liposomes in the range of from 90 to 120 nm, wherein all the operations are performed under aseptic conditions.

However, the method according to the prototype implies a compliance with certain conditions that may negatively affect a reproduction of the method and a pharmaceutical quality of the target product, while the created liposomal LP composition will not provide an optimal pharmacotherapeutic effect.

Firstly, the prototype proposes three different solvents to dissolve LP, ePC, and CHOL (including a highly toxic methanol), thereby complicating the implementation of the method, and the unpredicted control of residual solvents may negatively affect the product's pharmacopoeial quality and harmlessness.

Secondly, the matter of creation of the liposomal composition on the basis of the pH 5.5 phosphate buffer that is proposed in the prototype does not meet the physiological pH value and does not facilitate creation of the active acidic form of latanoprost.

Thirdly, the prototype asserts the extrusion of a structurally heterogeneous system produced by transporting only hydrophobic components to the aqueous solution of the dry film under indefinite pressure that may negatively affect the product's standardization.

Fourthly, the prototype proposes introduction of the large amount of CHOL (from 10% to 40% by weight of the liposomes, i.e. the ePC+LP mass) that facilitates increase of rigidity of the membrane and polydispersity of the liposome sizes.

Fifthly, the method algorithm does not imply a stable quality of the created liquid composition during storage. The prototype interprets the product's stability only on the basis of preserving the average size of the liposomes (from 82 to 89 nm) in absence of other important parameters of the pharmaceutical quality being a dispersion of sizes, an oxidation index and a number of impurities. Therewith, a contact of the liposomes with the aqueous phase will definitely case the oxidation of the lipids and re-formatting of sizes of vesicles. It should be also noted that storage periods (during 6 months at 4° C. or during a month at 25° C.) do not meet the pharmacoeconomic standards for drugs.

Sixthly, a pharmacological quality is not proven correctly for the liposomal LP composition created according to the prototype (as for other liposomal products of LP discussed above), since the declared antihypertensive and antiglaucomic activity has been evaluated for healthy normotensive animals.

Generally, all the mentioned information reduces the efficiency of the prototype method regarding a process of its implementation, as well as stability and quality of the target product being the pharmacologically active liposomal composition of LP.

A task of the claimed invention is to provide a method for preparing a liposomal composition comprising LP with optimized operations that could provide an increase of the quality and stability of the target product, and to prepare a liposomal composition of LP by this method, the composition having an optimal formulation and a prolonged pharmacological action, and is adequate for use as a therapeutic agent for treatment of ophthalmic hypertension and glaucoma.

The posed task is resolved by the fact that in the method for preparing the liposomal composition comprising LP, which includes creating a mixture of solutions of ePC, LP, and CHOL in organic solvents, vacuum drying thereof, emulsifying in a buffer solution, and homogenizing, according to the invention, when creating the mixture of solutions, ePC, LP, and CHOL are dissolved in ethyl alcohol, a solution of DPPG in a mixture of ethyl alcohol and chloroform is added to the mixture, a mass ratio of ePC:DPPG:LP being 1:0.02-0.04:0.03-0.05 and a mass ratio of ePC+DPPG+LP: CHOL being 1:0.02-0.04 are used, the dried film is emulsified in a lactose solution in pH 7.1 buffer under a mass ratio of ePC:lactose being 1:2, and the homogenization is performed at a stepwise pressure increase from 300 to 800 at followed by a sterilizing filtration and a freeze drying.

The posed task is also resolved in that the implementation of the novel method results in the creation of the identified liposomal composition comprising LP, ePC, and CHOL, wherein, according to the invention, DPPG and lactose are present, and the mass ratio of LP:ePC:DPPG:CHOL:lactose is 1:20.0-30.0:0.60-0.75:0.50-0.90:40.0-60.0.

According to the task of the invention, for the created liposomal composition of LP the pharmacological activity in ophthalmology is established: prolonged antihypertensive action in case of OG and antiglaucomic effect.

The following examples illustrate a possibility of implementation of the claimed method and preparation of the target product by this method, the product is the liposomal composition of LP, and the example of the prototype method for comparison.

Example 1—The claimed subject matter. A precise weighed quantity of 400 mg of LP (in terms of a 100% substance [e.g., Cayman Pharmas.r.o., Czech Republic]) is dissolved in 100 ml of ethyl alcohol under stirring and is filtered through a membrane filter pore size of 0.45 μm. A precise weighed quantity of 12.0 mg of ePC (in terms of a 100% substance [e.g., Lipoid GmbH, Germany]) is dissolved in 150 ml of ethyl alcohol under stirring and is filtered through the membrane filter having the pore size of 0.45 μm. A precise weighed quantity of 240 mg of DPPG (in terms of a 100% substance [e.g., Lipoid GmbH, Germany]) is dissolved in 100 ml of a mixture of ethyl alcohol and chloroform (a volumetric ratio is 1:9), afterwards it is filtered through the membrane filter having the pore size of 0.45 μm. precise weighed quantity of 360 mg of CHOL (in terms of a 100% substance [e.g., Sigma-Aldrich]) is dissolved in 100 ml of ethyl alcohol and is filtered through the membrane filter having the pore size of 0.45 μm.

The prepared solutions are transferred to a rotary evaporator and the solvents are removed under vacuum at a temperature of 39-41° C. and an ultimate pressure of 10-15 at until a dried thin film is produced. After completion of the drying process, an inert gas is transmitted to a flask of the evaporator during 30-40 min.

A precise weighed quantity of 24.0 g of lactose monohydrate (Ph.Eur.) in terms of a 100% substance at a temperature of 50-60° C. and under stirring is dissolved in 400 ml of a phosphate buffer pH 7.1 (Ph.Eur.) and filtered through a membrane having a pore diameter of 0.22 μm (0.06 g/ml of lactose).

The produced dried film is quantitatively taken off from the flask walls of the evaporator by means of 400 ml of the lactose solution in the pH 7.1 phosphate buffer under stirring during 60 min on an orbital mixer at 100-120 RPM until a homogeneous emulsion is produced.

The emulsion is transferred to a reactor of a high-pressure homogenizer (e.g., M 110P Microfluidizer Processor, Microfluidics) and is exposed to dispersing at a temperature 40-52° C. with a stepwise pressure increase from 300 at during 3 cycles to 800 at during 7 cycles. At the end of the dispersing process the particle size of the emulsion (Malvern Zetasizer NanoZS) does not exceed 220 nm.

After the homogenization is completed, the emulsion is filtered through the hydrophobic membrane having a pore diameter 0.22 the LP content therein is defined, it is exposed to a sterilizing filtration under aseptic conditions and poured into glass bottles in a dosed fashion (the LP content is 0.5 mg per bottle).

The emulsion is subjected to freeze drying in the bottles (e.g., Martin Christ-2-6-D, USA) according to a program that implies an intensive freezing, basic drying, and final drying. Upon drying, the bottles with the frozen-dried product are sealed under the inert gas atmosphere. The pouring, freeze drying, and sealing processes are performed under aseptic conditions.

The target product is a frozen-dried amorphous mass having a white color with a yellowish tinge and a characteristic odor.

The operations and measures of the claimed method in Examples 2-15 are performed according to the Example No. 1. Changes of the process parameters are stated in Tables 1 and 2. It should be noted that the Example No. 13 intentionally does not imply the operation of introducing the DPPG for detection in comparison with other examples of influence of this component both on reproduction of the method and on the quality of the created product.

Example No. 16—the prototype according to [15]. A precise weighed quantity of 400 ml of the LP (in terms of a 100% substance [Cayman Pharmas.r.o., Czech Republic]) is dissolved in 200 ml of acetonitrile. A precise weighed quantity of 4.65 g of ePC (in terms of a 100% substance [LipoidGmbH, Germany]) is dissolved in 300 ml of a mixture of chloroform and methyl alcohol (the ratio is 2:1 by volume). A precise weighed quantity of 510 mg of CHOL (in terms of a 100% substance, [Sigma-Aldrich]) is dissolved in 100 ml of a mixture of chloroform and methyl alcohol (the ratio is 2:1 by volume). The ePC and cholesterol solutions are combined and the LP solution is added to this mixture maintaining the temperature of 40° C.

The created mixture of solutions is transferred to the rotary evaporator and the solvents are removed under vacuum at a temperature of 39-41° C. After production of the dry film, the rotation of the evaporator is continued under a low pressure during 60 min. The dried film is quantitatively taken off from the flask walls of the evaporator by means of 400 ml of the pH 5.5 phosphate buffer (Ph.Eur.). The produced suspension is extruded through the polycarbonate filters having a pore diameter of 0.22 μm (the Evonicand Transferra Nanosciences extruder, previous company name is Northvern Lipids Inc., Canada). The extrusion is performed during 10 successive cycles under a continuous pressure of 800 atm. At the end of the extrusion process, the product particle size does not exceed 115 nm (Malvern Zetasizer NanoS). The entire procedure is performed under aseptic conditions in a laminar cabinet.

The target product according to the prototype is a semi-transparent solution having an adulterated milk color and a characteristic odor.

During identification and determination of quality parameters, the liposomal composition of LP prepared according to the Examples Nos. 1-14 by the claimed method was used in the form of emulsion reproduced by adding 0.5 ml of a sterile water for injections to the bottle with the frozen-dried product, while according to the Example No. 15 and the prototype method, a liquid product per se was used, which corresponds to the parenteral method of a potential pharmacotherapeutic use.

The efficiency of the claimed method in terms of the pharmaceutical quality of the created liposomal composition is confirmed by results of the qualitative and quantitative identification of LP, ePC, DPPG, and CHOL, as well as proofs of a liposomal status of the target product using a number of independent physical and chemical methods, namely:

By a method of liquid chromatography with an evaporative light scattering detection (ELSD) on a PerfectChrom 100 Diol column at a temperature of 55° C. with a mobile phase based on a mixture of n-hexane, 2-propanol, glacial acetic acid, and triethanolamine according to a chromatogram of the target product solution in the mixture of chloroform and methanol (20:80 vol.) using chromatograms of the solutions in methanol standard samples of ePC and DPPG for calibrating and comparing (identification and quantitative determination of ePC and DPPG);

By a liquid chromatography method on a SupelcoSi column with a protective cartridge at a temperature of 30° C. with a mobile phase based on a mixture of n-hexane and ethanol (94:6 vol.) with a spectrophotometric detection at a wavelength of 409 nm, according to chromatograms of the solutions in the mixture of n-hexane and ethanol (94:6 vol.) of a dry residue of a methanol extract produced from the dried aqueous emulsion of the target product itself or after gel filtration thereof on the column with Sephadex G-25 (eluate—0.9% solution of sodium chloride) controlling the output of liposomes according to absorption at a wavelength of 540 nm. For the calibration and comparison, a peak area of the LP on the chromatogram of the solutions of the standard LP sample in the mixture of n-hexane and ethanol (94:6 vol.) was used (the quantitative determination of the LP in the product and a degree of the LP encapsulation);

By a thin-layer chromatography method on a Supelco Silicagelon TLC AL plate according to the chromatogram of the target product solution in the mixture of methanol and water (80:20 vol.), at which blots of ePC, DPPG, and CHOL are present at the level of main blots of the standard ePC, DPPG, and CHOL samples on the chromatograms of solutions in ethyl alcohol, using an aqueous solution of a mixture of phosphoric acid and copper sulfate for imaging, and a mixture of chloroform, methanol, and water as a mobile phase (65:30:5 vol.) (identification of ePC and DPPG and quantitative determination of CHOL);

By a thin-layer chromatography method on a Supelco-Silicagelon TLC AL plate according to the chromatogram of the target product extract in the mixture of methanol and water (80:20 vol.), at which blots of lisoderivatives of ePC and DPPG are present at the level of main blots of the standard lisoPC and lisoD-PPG samples on the chromatograms of solutions in alcohol, using an aqueous solution of a mixture of phosphoric acid, glacial acetic acid, and copper sulfate for imaging, and a mixture of chloroform, methanol, and water as a mobile phase (65:30:5 vol.) (determination of the oxidation index of lipids and impurities to evaluate the stability of the liposomes);

By a gaseous chromatography method on a DB-624 column (USA 149855H) according to a target product chromatogram in a presence of an internal standard (a mixture of N,N-dimethylformamide with propanol-1) using peak areas of ethyl alcohol, methanol, chloroform, and acetonitrile for comparison on the chromatograms of the internal standard solution and standard samples of the corresponding solutions (determination of residual organic solvents);

By a laser diffraction method on a Malvern Zetasizer NanoZS appliance of a target product emulsion (determination of sizes of liposomes and particle size distribution);

Determination of pH parameters and osmolality of the target product emulsion (compliance with the requirements of the functional use of ophthalmologic drugs).

The above-mentioned methods were also used for the qualitative and quantitative identification of the product prepared according to the prototype method.

According to the results of the physical and chemical analyzes (Table 3), the claimed method provides identity and pharmaceutical quality of the target product being the liposomal composition comprising LP, namely:

According to the data of the thin-layer and liquid chromatography, a nativeness and a quantity of the components used for implementation of the method have been reliably confirmed in the target product, which correspond to the ones for the standards of LP, ePC, DPPG, and CHOL;

LP is quantitatively included to the liposomes with the encapsulation degree of from 92 to 100%;

A robust average size of the liposomes (220 nm) in the emulsion prior to the freeze drying and after reproduction from the frozen-dried target product is accompanied by almost monodispersity of their size distribution (92-100%) and low oxidation index;

According to the results of determination by the gaseous chromatography method, the content of the residual used solvents in the target product is less than the acceptable level that is established by the pharmacopoeial requirements for the drugs;

The pH value of the emulsion is stable (pH 7.1) and corresponds to the physiological norms for this parameter in vivo;

The osmolality parameter of the emulsion meets the pharmacopoeial requirements for ophthalmologic drugs.

It should be noted that the optimal pharmaceutical quality with generalization of all the parameters is peculiar to the target product created by the claimed method according to the Examples No. 1-3. The implementation of the claimed method with consideration of differences of the ratio of components (Examples 4-8, 9), including the omission of DPPG (Example 13), and elements of the processing (Examples 9-12, 14-15), or with consideration of a combination of these factors, as well as the implementation of the prototype method (Example No. 16) cause a negative distortion of the pharmaceutical quality parameters (Table 3), namely:

reduction of the encapsulation degree of the LP to liposomes (2-8% in the Examples No. 4-15 and 5-7% in the prototype);

reduction of the average size of the liposomes (5-15% in the Examples 11 and 12 and 56% in the prototype) that is an undesirable factor when administering the product into the ocular structures;

a non-homogeneity of the liposome dispersity in terms of sizes (up to 20% in the Examples 8, 14 and in the prototype);

raise of the oxidation index of the liposomal product (14-38% in the Examples Nos. 4-15 and 38% in the prototype);

the pH value of 5.5 according to the prototype and the Example 11 that does not meet the physiological norms for this parameter in vivo;

a tendency towards the increase of the content of the residual solvents in the Examples 4 and 14 (the content of the ethyl alcohol), as well as in the prototype—the content of the ethyl alcohol, chloroform, and acetonitrile by 3, 4, and 2 times respectively;

a relative reduction of the emulsion osmolality (20-40 mOsmol/g to a lower limit of the pharmacopoeial norm being 280 mOsmol/g) for the Examples 10 and 11 and for the prototype.

It should be emphasized that most of said negative changes also relate to the product of the Example 13 that was created without use of the DPPG.

Said important advantages of the pharmaceutical quality of the product according to the Examples Nos. 1-3 match to the optimized parameters of the implementation of the claimed method (Table 3) as compared to the process parameters, which are provided by other examples and the prototype method (Example 16), in particular:

involvement of the DPPG to the method implementation as a component of the target product (absence of the DPPG in the Example 13 and in the prototype or reduction its ratio relative to the ePC in the Example 4 has caused the deterioration of the pharmaceutical quality of the product in terms of the parameters of the LP encapsulation, dispersity of sizes of the liposomes, and the oxidation index);

optimization of the used ratios between LP with ePC, as well as CHOL, and the sum of the component (ePC+DPPG+LP), which form the liposomes (their relative reduction or increase in the Examples 5-7,9 and the prototype leads to the deterioration of the pharmaceutical quality of the product in terms of the LP encapsulation, sizes of the liposomes, and the oxidation index);

preferential use of ethyl alcohol or its mixture with chloroform (the latter is for DPPG only) to dissolve the components. Use of the acetonitrile to dissolve LP and the mixture of chloroform and methyl alcohol for ePC and CHOL in the Examples 9 and 10 similarly with the prototype reduces the LP encapsulation and increases the content of the residual solvents;

use of the lactose solution in the pH 7.1 phosphate buffer during the process of emulsifying the film. Therewith, the emulsifying by the lactose solution in the pH 5.5 phosphate buffer according to the Example 11 and the pH 5.5 phosphate buffer according to the prototype No.

16 leads to the deterioration of the product quality in terms of correspondence with the physiological pH values in vivo;

conduction of dispersing with a successive pressure increase under 300 at (1-3 cycle) and 800 at (4-7 cycle). Changes of the pressure parameters according to the Examples Nos. 7, 12, 14 and to the prototype (800 at during the entire process) negatively affect a number of parameters of the pharmaceutical quality, in particular, the LP encapsulation and size of the liposomes;

involvement of the freeze drying operation, while its intentional comparative omission (Example No. 15) or non-provision (No. 16—the prototype) causes the increase of the oxidation index and of the residual solvents.

Therefore, the claimed method as implemented according to the Examples No. 1-3 enables to create the liposomal composition comprising LP as the product having the high pharmaceutical quality with its illustrative characteristics being established according to the validated methods.

Based on the reliable data regarding identification and content of LP, ePC, DPPG, and CHOL in the product, the formulation of the composition prepared by the claimed method and by the prototype method has been calculated in terms of a mass ratio of the components (Table 4).

According to the task of the invention, the quality of the created liposomal composition of LP has been evaluated in terms of the parameters of the level and the duration of the pharmacological effect as to the TOP and signs of the optic neuropathy. The ophthalmologic specificity of the studies corresponds to the task of the invention meaning the evidentiality of the creation of the target product with the function of the prolonged pharmacological activity in case of OG and glaucoma.

In order to meet bioethical norms for the animal handling and minimizing their number in experiments [24], the pharmacological studies have utilized separate illustrative examples of the liposomal composition comprising LP. In order to provide an optimal balance between compliance to the mentioned norms and the evidentiality of the evaluation of the pharmacological activity of the composition created by the claimed method, examples having the highest pharmaceutical quality (Examples Nos. 1-3) have been studied, as well as the Examples Nos. 10, 13, 15 for comparison, under an unconditional assessment of the effect of the product created according to the prototype method (Example No. 16).

The ophthalmologic studies have been carried out on mature male rabbits of a "Chinchilla" breed 1 year old with a body mass of from 2.5 to 3 kg, which were in vivarium conditions and received a standard diet and drinking water ad libitum. Randomization of the animals was carried out on the basis of evaluation of their overall health condition, control of a condition of eyes, retina, and IOP. The experimental groups included 8 animals per group, n =8. Prior to the experiment, the IOP of the randomized animals were within a normal range (from 12 to 16 mm Hg) with an improbable difference that provides evidence of a validity of formation of the animal groups. The IOP level was determined with an applanate tonometer having a 10.0 g plunger.

When modeling the IOP pathology according to [25,26], an anterior chamber of the eyes of the animals was injected with 0.1 ml of 0.3% of carbomer in isotonic solution under general anesthesia of a 10% thiopental sodium solution in a dose of 1 ml/kg. The OG formation occurred at 14th day after the first carbomer injection, the stable OG with glaucoma was formed in a week after the second carbomer administration.

The pharmacological quality of the liposomal composition of LP was determined in terms of its effect in the form of ophthalmic drops and subconjunctival injections.

The frozen-dried products according to the claimed method were used in the form of emulsion created by introducing 0.5 ml of the sterile water for injections into the bottle and by shaking during 3-5 min. The liquid products according to the Examples No. 15 (the claimed method) and No. 16 (the prototype method) were used per se after preparation. According to the established pharmaceutical quality parameters (Table 3), the LP concentration in the emulsion of the products according to all of the examples was about 1 mg/ml.

Instillation of the liposomal form of LP was performed by one drop into both eyes of the rabbits, at every day's evening during the entire follow-up period. In order to conduct an objective evaluation of the pharmacological effect, the drug "Lanotan", ophthalmic drops (AO "Farmak", Ukraine) was used as the analogue in terms of the functional activity.

The subconjunctival administration of the liposomal composition of LP was carried out by injecting 0.1 ml of the emulsion under local anesthesia with 1% alcaine solution.

The IOP monitoring was carried out at key steps of the IOP determination for each of the animal groups (intact control, pathology control after reproduction of the model, after the subconjunctival injection or instillation) within time periods that prove the dynamics of the level and duration of the pharmacological effect of the liposomal composition of LP (Tables 5-7).

At the end of the IOP monitoring period, the animals were withdrawn from the experiment in anesthesia condition (1 ml/kg of the 10% thiopental sodium solution) by an air embolism method. In order to conduct a histomorphologic and biochemical evaluation of the retina, the eyes were enucleated on ice at 0-5° C.

During pathomorphological studies, the eyes were fixed in neutral 10% formalin and paraffin blocks were received according to the standard technique. Cut-offs were stained with hematoxylin-eosin and examined on a light microscope. In the retina equatorial zone, a condition of neurons in a main ganglionic layer and of bipolar cells of an internal nuclear layer was evaluated within a field of view under magnification of 100× and 600×.

During the biochemical studies, a content of neurotoxicity markers, which are glutamate and malondialdehyde (MDA), was determined in an ocular homogenate by standard methods [27-29].

Results of the experimental studies were processed by means of non-parametric methods of statistical analysis using the Statistica 5.5* package.

According to the standards of development of potential drugs, the study of the pharmacological activity of the novel products was preceded by establishment of their usage safety that implied a confirmation of its ophthalmologic safety in terms of the specificity of the target product of the claimed method.

The ophthalmologic safety of the instillations and subconjunctival injections of the liposomal composition of LP has been established within separate groups of rabbits (n=8) having the ophthalmoscopically and visually confirmed normal intact condition of eyes.

BRIEF DESCRIPTION OF DRAWINGS

Inspection results are illustrated by drawings, which depict the following.

When studying an acute and chronic ophthalmic toxicity of the drops, the product emulsion was instilled into the right eye of the rabbits each 15 minutes during 6 hours and once a day in the evening during 30 days, respectively. The left eye (control) was instilled with the physiological solution being a 0.9% sodium chloride solution. The eye condition was evaluated by means of the Draize test (in balls) in terms of an appearance and a conjunctival test [30].

After instillation of all the products, no changes of the condition of the cornea, conjunctiva, iris, as well as edema and eye discharges have been detected (0 balls for all) that provides evidence of an absence of the acute and chronic ophthalmotoxicity of the liposomal composition of LP in case of the drop administration.

Figure 1:
FIG. 1 is a condition of the anterior chamber of the rabbit eye in an hour after the subconjunctival injection with the liposomal composition of LP prepared by the claimed method (Example No. 3).

Upon the subconjunctival injection of 0.1 ml of the product emulsion prepared by the claimed method, in an hour, no changes of the eye condition in 4 of 8 animals of the group have been detected. The condition of the tested eye of the rabbits from other groups, according to the Draize test, was, in average: cornea—0.4; conjunctiva—0.4; iris—0.2; edema—0.4; discharges—0 balls (FIG. 1).

Figure 2:
FIG. 2 is a condition of the anterior chamber of the rabbit eye in an hour after the subconjunctival injection with the liposomal composition of LP prepared by the prototype method (Example No. 16).

In an hour after the subconjunctival injection of 0.1 ml of the product emulsion according to the Example No. 15 and to the prototype No. 16, the Draize test has shown the following: cornea—1; conjunctiva—1; iris—1; edema—1; discharges—0 balls (FIG. 2).

Figure 3:
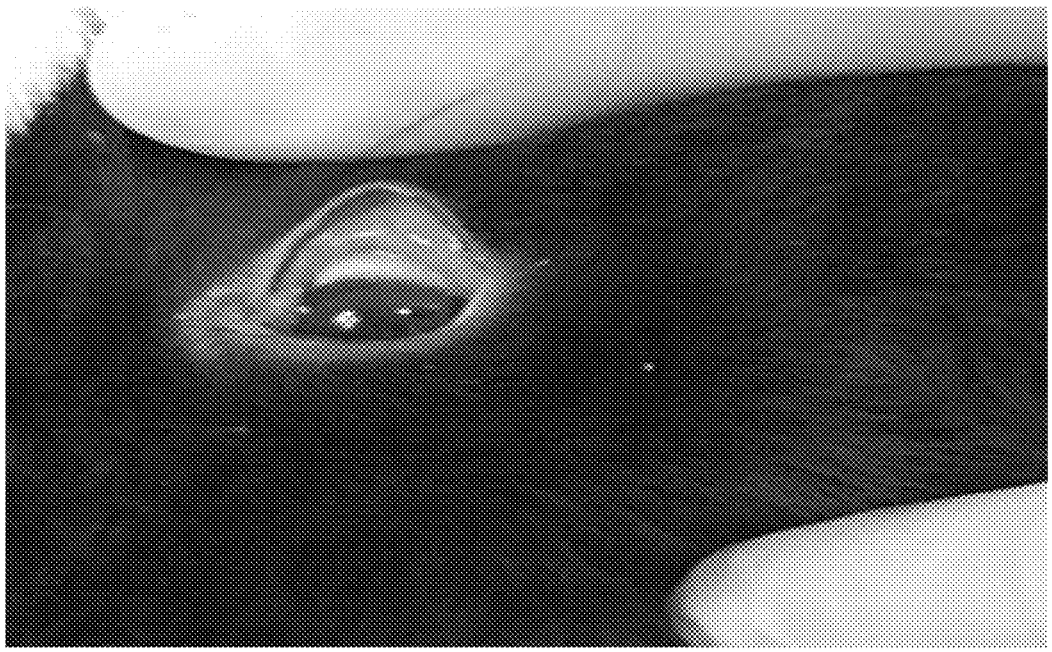
FIG. 3 is a condition of the anterior chamber of the rabbit eye in a day after the subconjunctival injection with the liposomal composition of LP prepared by the claimed method (Example No. 1).
Figure 4:
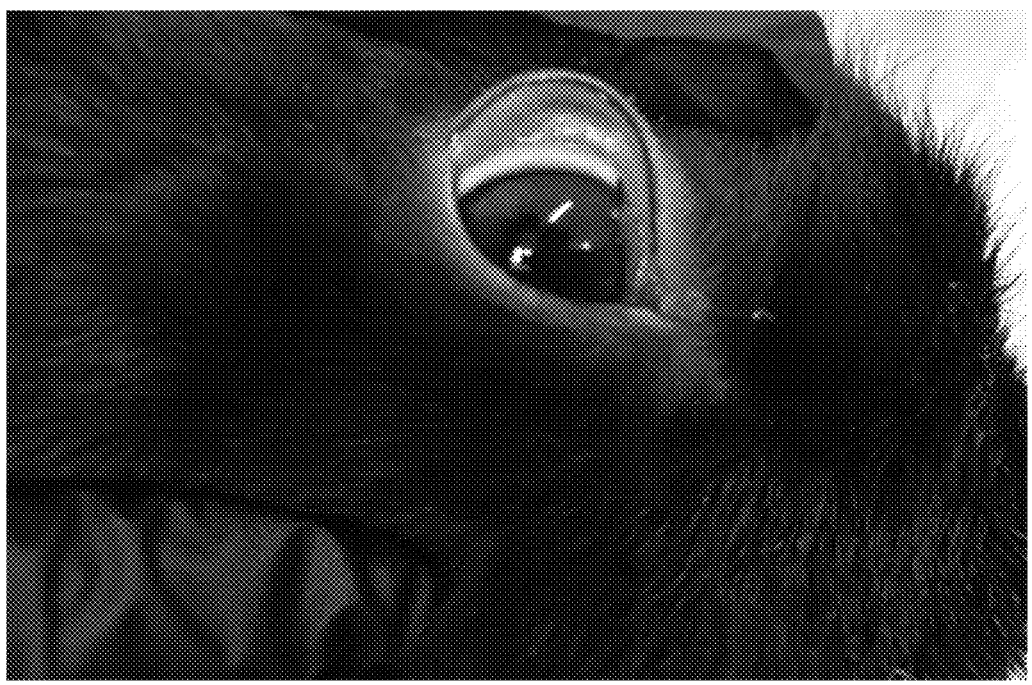
FIG. 4 is a condition of the anterior chamber of the rabbit eye in a day after the subconjunctival injection with the liposomal form of LP prepared by the prototype (Example No. 16).
Figure 5:
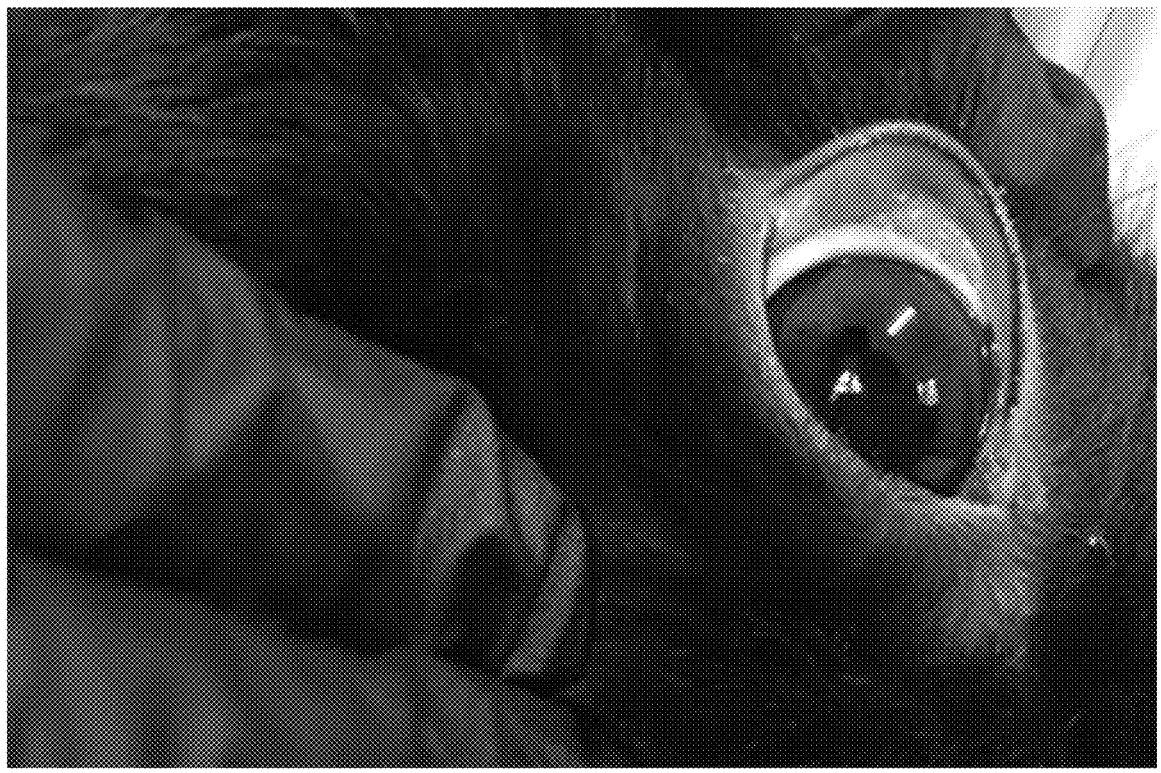
FIG. 5 is a condition of the anterior chamber of the rabbit eye in a day after the subconjunctival injection with the liposomal form of LP prepared by the claimed method (Example No. 15).

In a day after the subconjunctival injection, the condition of the tested eye in most of the animals was without any specific changes (0 balls for all) (FIG. 3). Signs of an irritating effect onto the cornea and conjunctiva with a minor edema were seen in 2 rabbits after injection of the product according to the Example 15 and according to the prototype (FIGS. 4, 5), although such changes were statistically unreliable in terms of the Mann-Whitney test for both the control and tested eyes.

The absence of significant negative changes in the eye condition after the instillations and subconjunctival single injections of the emulsion provides the evidence regarding the ophthalmic safety of the liposomal composition of LP with optimal parameters of harmlessness for the product of the claimed method.

Taking into consideration a non-triviality of the use method being the subconjunctival injection and the novelty of the liposomal composition of LP as a potential drug, the ophthalmologic safety has been confirmed by a demonstrative method of the optical coherent tomography (OCT) (tomograph SOCT Copernicus REVO NX 700 Software-Version 9.0 2018).

In order to provide a prognostic clinical perception of the information by the OCT, a condition of a conjunctival-limbal area of the anterior chamber of the eye was appreciated in the animals with the OG pathology directly after the subconjunctival injection and within distant terms (90 and 120 days, under the IOP dynamics according to the Table 6). Therewith, it should be noted that the OCT data after the subconjunctival injection of the liposomal LP product stated in the prototype was received exclusively for normotensive animals, thereby putting in a doubt their correct clinical correlation with the OG.

Figure 6:
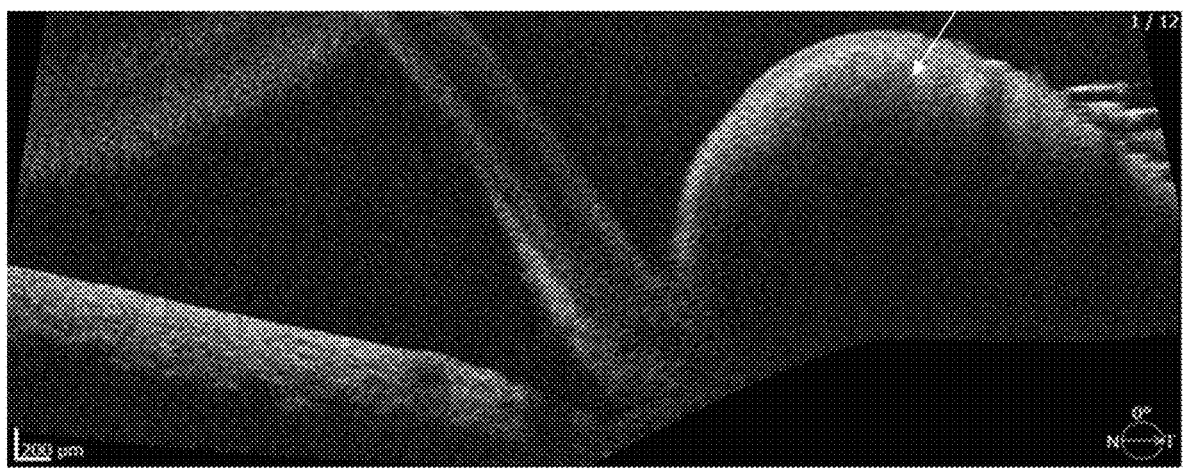
FIG. 6 is an OCT scan image of the anterior chamber of the rabbit eye having the ocular hypertension immediately after the subconjunctival injection with the liposomal composition of LP prepared by the claimed method (Example No. 1). The arrow indicates a site for the product administration. The regimen is Radial 7×7 mm ANTERIOR Multi B-scan.

Directly after the subconjunctival injection of the liposomal composition of LP to the rabbit with the OG, a change of the conjuctiva's relief in the form of a gangliform invagination was noted (FIG. 6, the product according to the Example No. 1) that provides evidence of a targeted introduction of the product emulsion to the conjuctiva's tissue. On top of the invagination, the sclera is not visualized, the connective-tissue stroma of the conjuctiva has a mixed OCT-signal, but the structure of the conjuctiva's epithelium is not changed.

Figure 7:
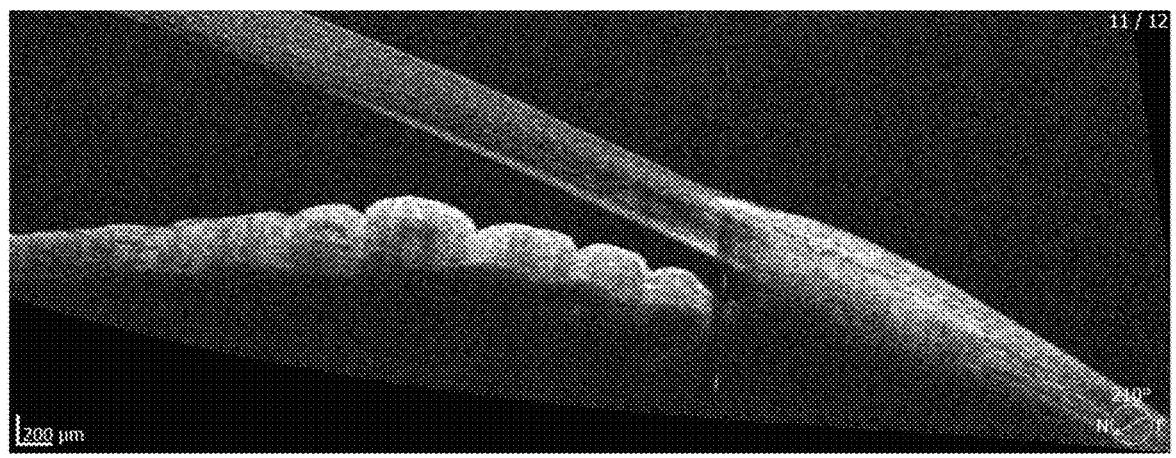
FIG. 7 is an OCT scan image of the anterior chamber of the rabbit eye having the ocular hypertension in 90 days after the subconjunctival injection with the liposomal composition of LP prepared by the claimed method (Example No. 1).
Figure 8:
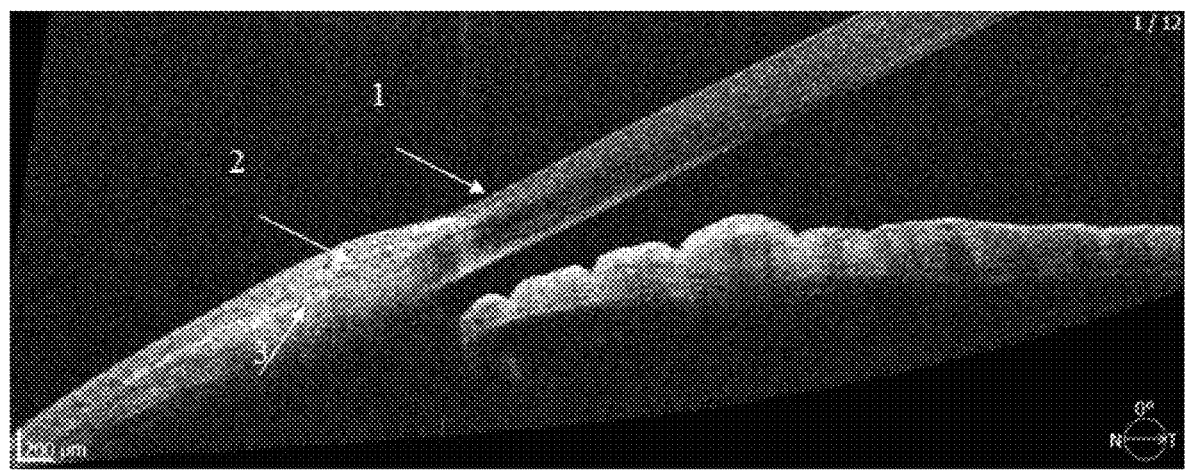
FIG. 8 is an OCT scan image of the anterior chamber of the rabbit eye having the ocular hypertension in 120 days after the subconjunctival injection with the liposomal composition of LP prepared by the claimed method (Example No. 1). The arrows indicate epithelium (1), connective-tissue stroma (2), sclera (3).

In 90 days after the subconjunctival injection of the product of the claimed method, the local deformation of the conjuctiva's relief is not significant anymore, the OCT scan lacks thinnings of the connective-tissue stroma and cicatrical changes in the epithelium and in the sclera (FIG. 7). At the 120th day of the follow-up, the OCT picture of the conjunctival-limbal area of the eye is normal: the tomogram is structural, three contrast layers (conjuctiva's epithelium, connective-tissue stroma, sclera) are well visualized with a high and moderate level of the OCT-signal, their boundaries are straight and continuous (FIG. 8).

Figure 9:
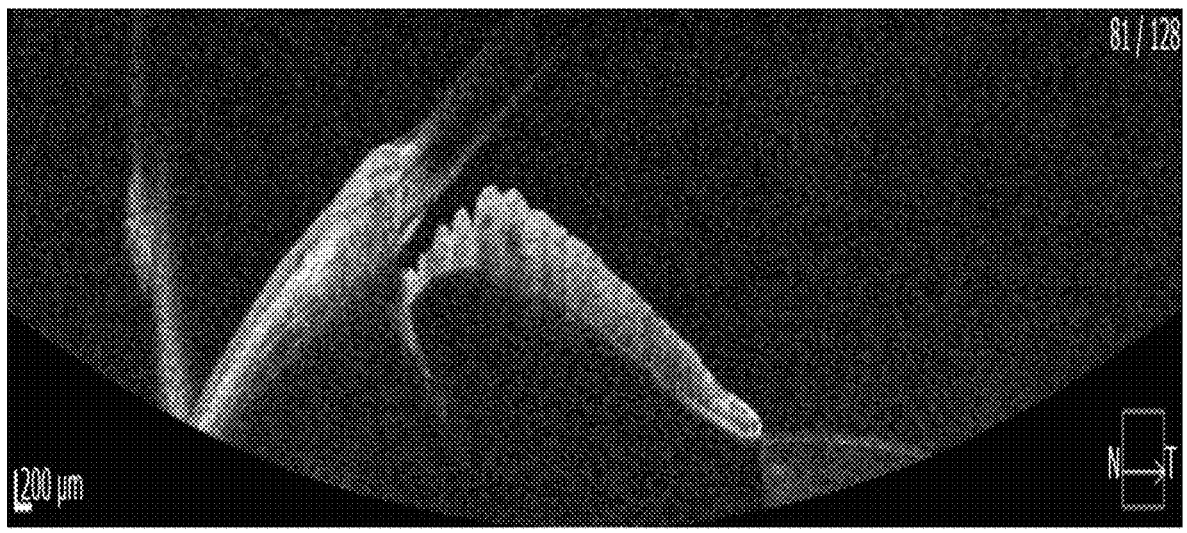
FIG. 9 is an OCT scan image of the anterior chamber of the rabbit eye having the ocular hypertension in 90 days after the subconjunctival injection with the liposomal composition of LP prepared by the prototype (Example No. 16).
Figure 10:
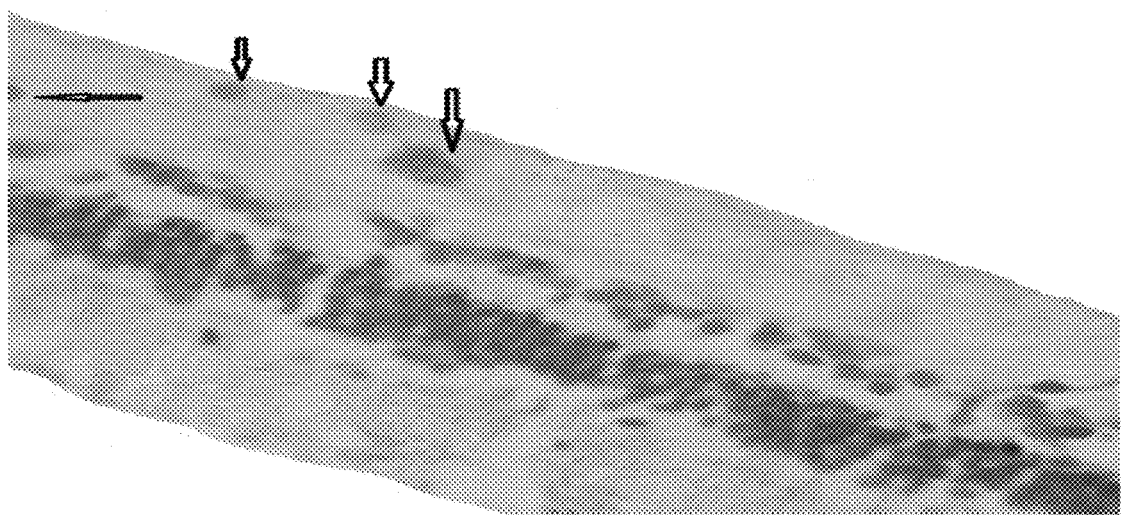
FIG. 10 is a retina of the rabbit having the stable OG and glaucoma (pathology control, 12 weeks). The extremely low density and non-uniformity of ganglion cells with plural dropout areas. The bipolar cells with dropout meshes of cells with a layer having a thin width with a reduced number of neurons. Magnification is 600×.
Figure 11:
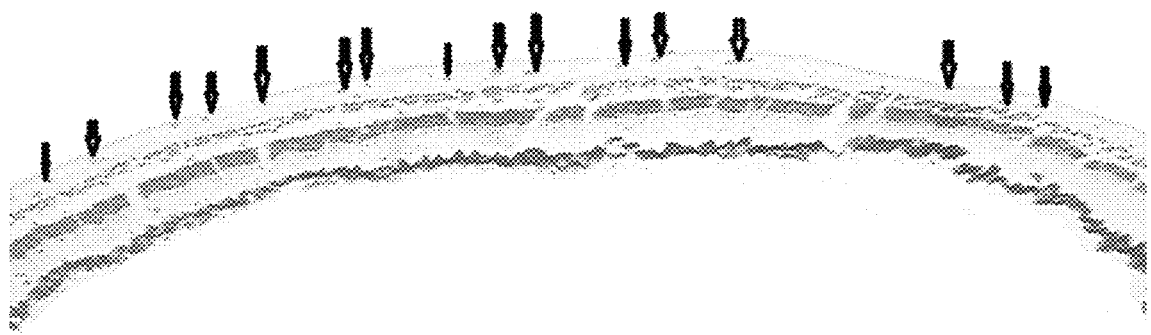
FIG. 11 is an influence of the subconjunctival injections of the liposomal composition of LP according to the claimed method (Example No. 1) onto the retina of the rabbit with the stable OG and glaucoma (the scheme in the Table 7, 12 weeks). The high density of the ganglion cells with a single dropout area. Layers of the bipolar cells having a uniform width (more than 3 layers of cells) are seen well in the entire image. Magnification is 100×.
Figure 12:
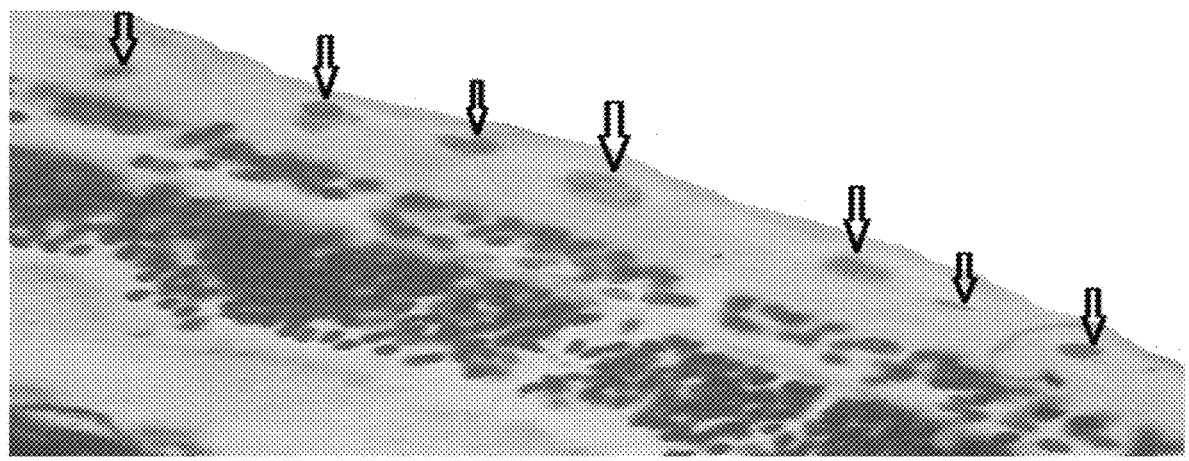
FIG. 12 is an influence of the subconjunctival injections of the liposomal composition of LP according to the claimed method (Example No. 1) onto the retina of the rabbit with the stable OG and glaucoma (the scheme in the Table 7, 12 weeks). The high density of the ganglion cells. Layers of the bipolar cells having a stable width are well seen in the entire image. Magnification is 600×.
Figure 13:
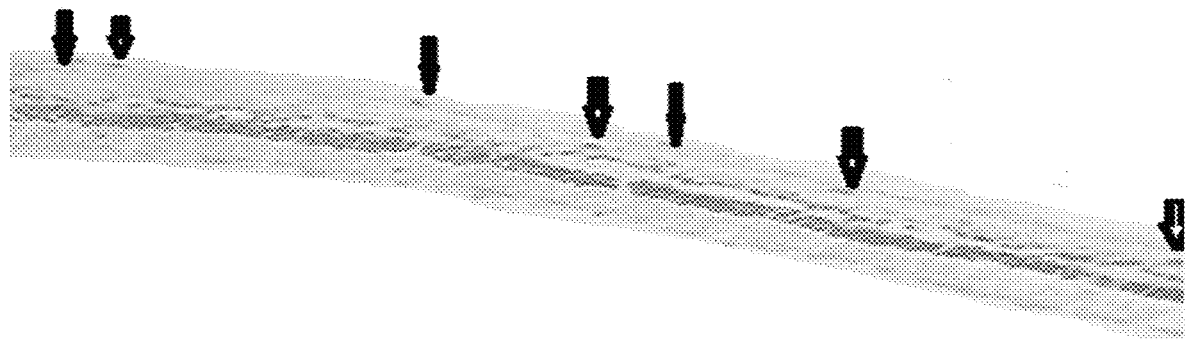
FIG. 13 is an influence of the subconjunctival injections of the liposomal composition of LP according to the prototype method (Example No. 16) onto the retina of the rabbit with the stable OG and glaucoma (the scheme in the Table 7, 12 weeks). The non-uniformity of arrangement and the relatively low density of the ganglion cells are seen. The internal nuclear layer is shortened to 1 series of the bipolar neurons having a cell-like dropout. Magnification is 100×.
Figure 14:
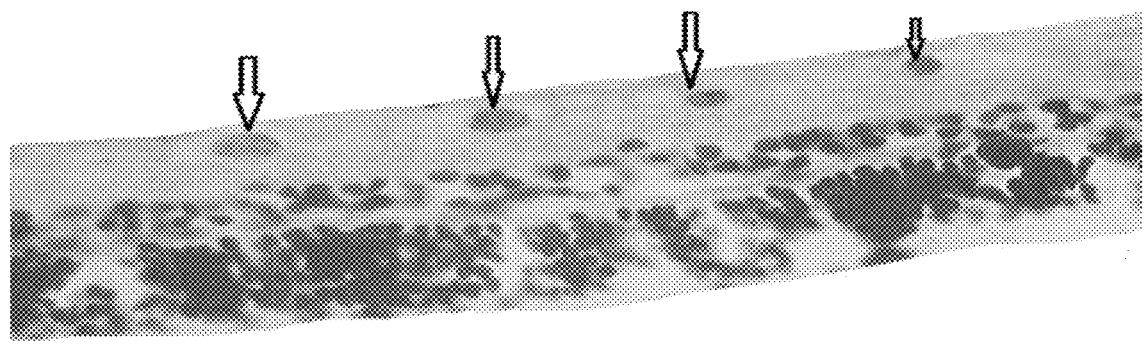
FIG. 14 is an influence of the subconjunctival injections of the liposomal composition of LP according to the prototype method (Example No. 16) onto the retina of the rabbit with the stable OG and glaucoma (the scheme in the Table 7, 12 weeks). The low density of the non-uniformly arranged ganglion cells is seen. Thinning of the layer of the bipolar cells with separate areas of their dropout. Magnification is 600×.

The OCT picture of the conjunctival-limbal area of the eye of the animals after the subconjunctival injection of the prototype composition within all terms is close to the one described above, however, at the 90th day after the injection, the intensity of the OCT-signal of the connective-tissue stroma is decreased (FIG. 9).

Results of the OCT studies not only has proven the absence of the negative changes of the conjuctiva's structure within distant terms after the subconjunctival injection of the liposomal composition of LP to animals with OG (the distant ophthalmic safety), but they also have visually demonstrated the delivery of the product to the predicted target zone of the pharmacological intervention.

The experimental results of the determination of the pharmacological activity of the liposomal composition of LP created according to the claimed method and to the prototype method are stated in the Tables 5-8. All the studied examples of the composition reveal the therapeutic effect as to the signs of the OG and glaucoma, however, the implementation of the claimed method particularly provides the creation of the product having more extended and high functional pharmacological activity:

1. At daily drop administration (Table 5), the liposomal composition of LP according to the claimed method (Examples 1-3) in the OG model provides an average 3.5 and 6.6 mm Hg decrease of the increased IOP at 1st and 12th week of the follow-up respectively, thereby exceeding the antihypertensive effect of the prototype product by 1.2 and 1.4 times, and by 1.2 and 1.8 times for the analogue drug with the same follow-up terms. The valuable level of the pharmacological activity of the installations of all of the products is seen during 12 weeks of the IOP monitoring, although only the liposomal composition of LP according to the Examples 1-3 almost provides the end normalization of the IOP up to the intact control.

It should be noted that the prototype does not discuss and does not propose the pharmacological activity of the product in case of the drop administration, thus, this effect was not expected, and its reveal in the LP composition according to the claimed method provides the advantage as to the creation of a "perfect" clinical compliance due to the possibility of combination of the drop and injection use.

2. At single subconjunctival injection administration (Table 6) in the OG model, the liposomal LP composition according to the claimed method exhibits a prolonged antihypertensive effect during all follow-up 12 weeks with the 6.2-7.3 mm Hg decrease of the IOP up to the intact control. The product of the prototype method is inferior to the claimed one in terms of the IOP decrease level in 3.3-5.5 mm Hg, as well as in terms of the duration of the antihypertensive effect, since starting from the 9th week after injection thereof a gradual recovery of the OG level at 0.5-2.5 mm Hg is noted.

3. In case of the experimental stable OG with glaucoma, the single subconjunctival injections of the liposomal LP composition according to the claimed method and to the prototype (Table 7) exhibit the prolonged antihypertensive effect during 6 weeks of the follow-up with the 33.0-39.3% and 14.4-20.0% IOP decrease, respectively, as compared to the pathology control (the initial TOP is 49% increased). The second injection of the LP composition according to the claimed method maintains the 34.4-39.3% IOP decrease with a tendency to normalize the ocular pressure up to the 12th week of the follow-up, while for the prototype, only 16.3% IOP decrease was registered at the 7th week with a slight gradual pressure increase up to the 12th week of the follow-up, i.e. the prototype is strongly inferior to the product of the claimed method in terms of the duration and the level of the effect.

4. The prolonged antihypertensive activity of the subconjunctival injections of the liposomal composition of LP (according to the Table 7, 12 follow-up weeks) is accompanied by the neuroprotective action according to the specific histomorphologic parameters of the retina, which provide an evidence of the antiglaucomic effect of the product of the claimed method with the advantages over the prototype product (Table 8):

preservation of the relative uniformity and high density of the neurons of the ganglionic layer that exceeds the one for the prototype by more than 2 and 3 times under small and large magnification, respectively, with almost no dropout areas of the ganglion cells, which exist under the prototype's influence (FIGS. 10-14);

preservation of the layer width and only insignificant reduction of the number of neurons within the layer of the bipolar cells as compared to the notable thinning of the width of this layer and the presence of areas with the reduced number of neurons under the action of the prototype (FIGS. 10-14).

In should be noted that the neuroprotective effect of the product of the claimed method is obvious when comparing to the histomorphologic picture of the animal retina with the stable OG (pathology control—FIG. 10) that, according to main criteria, corresponds to the human retina condition with glaucoma [30] with a non-uniform distribution and a sharp decrease of the density of neurons of the ganglionic layer with the dropout areas, reduction of the number of neurons, and thinning of the layer of the bipolar cells.

5. The liposomal composition of LP, on top of the prolonged antihypertensive action, develops the neuroprotective effect affecting the specific biochemical neurotoxicity markers being glutamate and MDA, while changes in their content in the retina provide evidence of the advantage of the product of the claimed method over the prototype product (Table 8):

40-43% reduction of the glutamate content in the retina relative to the pathology control with a tendency to normalize the parameter (only 2% increase relative to the intact control), while the same parameters of the prototype are 24% and 39% respectively;

37-42% reduction of the MDA content in the retina relative to the pathology control with a tendency to normalize the parameter (only 5% increase relative to the intact control), while the same parameters of the prototype are 25% and 33% respectively.

Generally, advantages of the pharmacological action of the liposomal composition of LP prepared by the claimed method have been demonstrated in comparison to the composition prepared by the prototype method in terms of the level and duration of the TOP reduction and recovery of histomorphologic and biochemical parameters of the retina condition, which provide evidence of the antihypertensive and antiglaucomic activity with a focus on the subconjunctival use that provides the prolonged effect. Said properties are inherent to all studied products of implementation of the claimed method, although the generalized high level of the pharmacological activity is provided by the liposomal composition of LP according to the Examples No. 1-3, for which the advantages of the pharmaceutical quality, which have been already described, are established.

This comparative conclusion has been made on the basis of the analysis of the parameters of the pharmaceutical and pharmacological quality, which have been established ex tempora after preparation of the liposomal composition of LP both by the claimed method and by the prototype method. Therewith, the reliable solution of the task of the invention is possible only after the long-term stability and the quality of the composition are confirmed, considering the provided target pharmaceutical purpose of the product and its pharmacotherapeutic use.

To this end, the stability of the quality of the liposomal LP composition prepared by the claimed method and by the prototype method has been determined when storing the target product during 6-12 months with a standard climate control.

Considering the long period of the works, the evaluation of the stability has been conducted for the illustrative examples of the liposomal composition of LP prepared by the claimed method (Examples 1 and 3 with the highest pharmaceutical quality established ex tempora, Examples 13 and 15—for comparison), as well as for the composition according to the prototype method (Example 16). The temperature regimen for storing the liquid-phase products according to the Examples Nos. 15 and 16-prototype (4° C.) is proposed in the description of the prototype, while for the frozen-dried products according to the Examples No. 1, 3, and 13 the Applicant has selected the temperature of –20° C.

Dynamics of the demonstrative parameters of the pharmaceutical and pharmacological quality when storing the liposomal LP composition (Table 10) provides evidence of a rather high stability of the product of the claimed method according to the Examples Nos. 1, 3, and 13 during 12 months, while essential changes of the parameters have been noted for the Examples Nos. 15 and 16-prototype at the 6th follow-up month already:

the content of the composition components relative to the initial one changes within the range of 1.1-4% only as compared to 5-26% for the Examples Nos. 15 and 16-prototype, while the largest deviations are seen for the CHOL. Thus, the mass ratio of the components (the formulation) remains stable that does not differ from the one for the product ex tempora (Table 4);

the sum of non-identified impurities in the product raises by 1.6 times, while it raises by 4 and 5 times for the Examples Nos. 15 and 16-prototype respectively;

the oxidation index remains almost unchanged, while it has 20% and 34% increase for the Examples Nos. 15 and 16-prototype respectively;

the dispersity profile has only 5-7% change, and almost retaining the initial size of the liposomes, while the proportion of the liposomes of the initial size for the Examples Nos. 15 and 16-prototype is not more than 50-78% with appearance of up to 30% of small liposomes. It should be noted that the prototype being the only one confirmation of the product's stability proposes only retention of the liposomes of a certain size (namely, 88 nm) leaving alone the appearance of the significant proportion of the liposomes of other sizes (up to 50%) during storage;

the prolonged antihypertensive activity of the single subconjunctival injection of the composition is 2.7% reduced, while the decrease of the effect regarding the IOP reaches 9-27% and 23-33% for the Examples Nos. 15 and 16-prototype respectively;

the normalizing influence of the composition onto the content of the neurotoxicity markers being glutamate and MDA in the retina is 2.1% and 0.5-1.2% reduced respectively, while these parameters of the antiglaucomic activity are 12.3%-10.1% and 4.2%-87.1% decreased for the Examples Nos. 15 and 16-prototype respectively.

The data of the conducted comparative analysis confirms the liposomal identity, stability of the formulation and of the pharmaceutical and pharmacological quality of the liposomal composition of LP prepared by the claimed method when storing during 12 months (Table 10). The composition according to the prototype, as well as the product of the claimed method No. 15, are not stable, have significant changes of the formulation and quality parameters already on the 6th month of the follow-up.

Generally, the highest quality is peculiar to the liposomal composition of LP that is created by the claimed method under compliance with the parameters, which are defined by the Examples 1-3 and differ from the ones provided by the prototype method, namely: when creating the mixture of the solutions, LP, ePC, and CHOL are dissolved in ethyl alcohol, the DPPG solution is introduced into the mixture of solutions in the mixture of ethyl alcohol and chloroform, the mass ratio of ePC:DPPG:LP being 1:0.02-0.04:0.03-0.06 and the mass ratio of ePC+DPPG+LP:CHOL being 1:0.02-0.04 are used, a emulsifying medium is the lactose solution in the pH 7.1 buffer at the mass ratio of ePC:lactose being 1:2, and the emulsion is dispersed at the stepwise pressure increase from 300 to 800 at followed by the sterilizing filtration and the freeze drying.

In case of the deviation from said parameters of the method (Examples 4-15 and the prototype being the Example No. 16), the desirable pharmaceutical quality of the target product being the stable liposomal composition of LP is not achieved (Tables 3 and 10).

Thus, the high pharmaceutical quality of the target product defines the functional pharmacological activity being the long-term and high antihypertensive effect in case of OG and the antiglaucomic action of the liposomal composition comprising LP, ePC, and CHOL, when providing parameters of its formulation, which are defined by the Examples Nos. 1-3 and differ from the ones for the composition created according to the prototype method, namely: the frozen-dried composition comprises DPPG and lactose, and the mass ratio of LP:ePC:DPPG:CHOL:lactose is 1:29.0-39.0:0.60-0.75:0.50-0.90:40.0-60.0.

The deviation from said parameters of the composition formulation (Examples 4-9 and the prototype being the Example No. 16, including the absence of the DPPG in the formulation being the Example No. 13) or its provision in the liquid-phase form (Example No. 15) reduces the pharmacological quality, namely the level and duration of the pharmacological effects.

The achieved optimal combination of the beneficial performance and elements of novelty of the method implementation with the reliable pharmaceutical identity and positive pharmacological properties of the target product proves the advantages of the claimed method in resolving the task that lies in the preparation of the liposomal drug comprising LP.

The stable liposomal composition of LP created according to the proposed method having the identified formulation, for which the ophthalmic harmlessness and pharmacological activity in case of OG and glaucoma have been established, beneficially differs from the liposomal product comprising LP prepared according to the prototype method. The high and prolonged pharmacological effect has been proven when using the created liposomal composition of LP in the form of drops and subconjunctival injection.

The stated information provides evidence of the expediency of use of the claimed method to prepare the stable and proper liposomal product comprising LP and incorporation of the liposomal composition of LP prepared according to this method as a drug having a rational compliance for the pharmacotherapy of OG and glaucoma.

TABLE 1

Parameters of the implementation of the claimed method for preparing the liposomal composition comprising LP and the prototype method for the ratios of the components of the composition being created, which were used when carrying out the process

| Example No. | ePC:DPPG:LP (wt.) | ePC + DPPG + LP:CHOL (wt.) | ePC:lactose (wt.) |
|---|---|---|---|
| The claimed method | | | |
| 1 | 1:0.02:0.03 | 1:0.03 | 1:2.0 |
| 2 | 1:0.04:0.05 | 1:0.04 | 1:2.0 |
| 3 | 1:0.03:0.04 | 1:0.02 | 1:2.0 |
| 4 | 1:0.01:0.03 | 1:0.02 | 1:2.0 |
| 5 | 1:0.016:0.03 | 1:0.01 | 1:2.0 |
| 6 | 1:0.02:0.03 | 1:0.05 | 1:2.0 |
| 7 | 1:0.02:0.025 | 1:0.04 | 1:2.0 |
| 8 | 1:0.05:0.03 | 1:0.03 | 1:2.0 |
| 9 | 1:0.02:0.03 | 1:0.01 | 1:2.0 |
| 10 | 1:0.02:0.03 | 1:0.03 | 1:2.0 |
| 11 | 1:0.02:0.03 | 1:0.03 | 1:2.0 |
| 12 | 1:0.02:0.03 | 1:0.03 | 1:2.0 |
| 13 | 1:n/u(DPPG):0.03 | 1:0.03 | 1:2.0 |
| 14 | 1:0.02:0.03 | 1:0.03 | 1:2.0 |
| 15 | 1:0.02:0.03 | 1:0.03 | 1:2.0 |
| The prototype method | | | |
| 16 The prototype | 1(ePC):n/u(DPPG):0.086(LP) | 1(ePC + LP):0.11(CHOL) | n/u lactose |

*n/u—the component is not used when creating the composition

TABLE 2

Parameters of the preparation of the liposomal composition of LP according to the claimed method and to the prototype method, which were used during carrying out the process (*n/u—not used in the process)

| | Example No. | | | | | | | | | | | | | | | |
|---|---|---|---|---|---|---|---|---|---|---|---|---|---|---|---|---|
| | The claimed method | | | | | | | | | | | | | | | 16-The prototype |
| | 1 | 2 | 3 | 4 | 5 | 6 | 7 | 8 | 9 | 10 | 11 | 12 | 13 | 14 | 15 | |
| Components involved into the method implementation: | | | | | | | | | | | | | | | | |
| LP | + | + | + | + | + | + | + | + | + | + | + | + | + | + | + | + |
| ePC | + | + | + | + | + | + | + | + | + | + | + | + | + | + | + | + |
| DPPG | + | + | + | + | + | + | + | + | + | + | + | + | n/u* | + | + | n/u* |
| CHOL | + | + | + | + | + | + | + | + | + | + | + | + | + | + | + | + |
| Lactose | + | + | + | + | + | + | + | + | + | + | + | + | + | + | + | n/u* |
| Dissolution medium For LP: | | | | | | | | | | | | | | | | |
| ethylalcohol | + | + | + | + | + | + | + | + | − | + | + | + | + | + | + | − |
| acetonitrile | − | − | − | − | − | − | − | − | + | − | − | − | − | − | − | + |
| For ePC: | | | | | | | | | | | | | | | | |
| ethylalcohol | + | + | + | + | + | + | + | + | + | − | + | + | + | + | + | − |
| chloroform + methyl alcohol 2:1 (vol.) | − | − | − | − | − | − | − | − | − | + | − | − | − | − | − | + |
| For DPPG: | | | | | | | | | | | | | | | | |
| ethyl alcohol + chloroform 1:9 (vol.) | + | + | + | + | + | + | + | + | + | + | + | + | n/u* | + | + | n/u* |
| For CHOL: | | | | | | | | | | | | | | | | |
| ethyl alcohol | + | + | + | + | + | + | + | + | − | + | + | + | + | + | + | − |
| chloroform + methyl alcohol 2:1 (vol.) | − | − | − | − | − | − | − | − | + | − | − | − | − | − | − | + |

TABLE 2-continued

Parameters of the preparation of the liposomal composition of LP according to the claimed method and to the prototype method, which were used during carrying out the process (*n/u—not used in the process)

| | Example No. | | | | | | | | | | | | | | | |
|---|---|---|---|---|---|---|---|---|---|---|---|---|---|---|---|---|
| | The claimed method | | | | | | | | | | | | | | | 16-The prototype |
| | 1 | 2 | 3 | 4 | 5 | 6 | 7 | 8 | 9 | 10 | 11 | 12 | 13 | 14 | 15 | |
| Emulsifying medium: lactose solution (0.06 g/ml) in the phosphate buffer | | | | | | | | | | | | | | | | |
| pH 7.1 | + | + | + | + | + | + | + | + | + | + | − | + | + | + | + | − |
| pH 5.5 | − | − | − | − | − | − | − | − | − | − | + | − | − | − | − | − |
| the pH 5.5 phosphate buffer solution | − | − | − | − | − | − | − | − | − | − | − | − | − | − | − | + |
| Emulsion dispersing parameters: A) Pressure, at: | | | | | | | | | | | | | | | | |
| 1-3rd cycle | 300 | 300 | 300 | 300 | 300 | 300 | 200 | 300 | 300 | 300 | 300 | 800 | 300 | 200 | 300 | 800 |
| 4-7th cycle | 800 | 800 | 800 | 800 | 600 | 800 | 800 | 800 | 800 | 800 | 800 | the entire process | 800 | 700 | 800 | the entire process |
| b) Particle size after dispersing, nm | ≤220 | ≤220 | ≤200 | ≤200 | ≤230 | ≤200 | ≤200 | ≤200 | ≤200 | ≤180 | ≤180 | <180 | ≤200 | <300 | ≤200 | <125 |
| Freeze drying of the emulsion after dispersing | + | + | + | + | + | + | + | + | + | + | + | + | + | + | n/u* | n/u* |

TABLE 3

Parameters of the identification and pharmaceutical quality of the liposomal composition prepared according to the claimed method and to the prototype method

| | Example No. | | | | | | | | | | | | | | | |
|---|---|---|---|---|---|---|---|---|---|---|---|---|---|---|---|---|
| | The claimed method | | | | | | | | | | | | | | | 16-The prototype |
| | 1 | 2 | 3 | 4 | 5 | 6 | 7 | 8 | 9 | 10 | 11 | 12 | 13 | 14 | 15 | |
| Identification of the components: | | | | | | | | | | | | | | | | |
| LP | + | + | + | + | + | + | + | + | + | + | + | + | + | + | + | + |
| ePC | + | + | + | + | + | + | + | + | + | + | + | + | + | + | + | + |
| DPPG | + | + | + | + | + | + | + | + | + | + | + | + | n/c | + | + | n/c |
| CHOL | + | + | + | + | + | + | + | + | + | + | + | + | + | + | + | + |
| Quantitative content of the components 1) The product-frozen-dried composition, mg/bottle: | | | | | | | | | | | | | | | | |
| LP (±0.02) | 0.50 | 0.50 | 0.52 | 0.50 | 0.51 | 0.50 | 0.48 | 0.50 | 0.49 | 0.50 | 0.47 | 0.50 | 0.51 | 0.50 | − | − |
| ePC (±0.15) | 15.0 | 10.0 | 13.0 | 14.9 | 17.5 | 15.1 | 19.2 | 15.1 | 14.9 | 15.0 | 13.82 | 15.0 | 15.2 | 14.87 | − | − |
| DPPG (±0.02) | 0.30 | 0.31 | 0.39 | 0.16 | 0.28 | 0.30 | 0.39 | 0.73 | 0.30 | 0.30 | 0.28 | 0.30 | n/c | 0.30 | − | − |
| CHOL (±0.02) | 0.45 | 0.42 | 0.30 | 0.32 | 0.19 | 0.61 | 0.77 | 0.49 | 0.16 | 0.45 | 0.42 | 0.44 | 0.47 | 0.40 | − | − |

TABLE 3-continued

Parameters of the identification and pharmaceutical quality of the liposomal composition prepared according to the claimed method and to the prototype method

| | Example No. | | | | | | | | | | | | | | | |
|---|---|---|---|---|---|---|---|---|---|---|---|---|---|---|---|---|
| | The claimed method | | | | | | | | | | | | | | | 16-The prototype |
| | 1 | 2 | 3 | 4 | 5 | 6 | 7 | 8 | 9 | 10 | 11 | 12 | 13 | 14 | 15 | |
| 2) The product-emulsion (without freeze drying), mg/ml | | | | | | | | | | | | | | | | |
| LP (±0.02) | – | – | – | – | – | – | – | – | – | – | – | – | – | – | 1.01 | 1.01 |
| ePC (±0.15) | – | – | – | – | – | – | – | – | – | – | – | – | – | – | 29.93 | 10.70 |
| DPPG (±0.02) | – | – | – | – | – | – | – | – | – | – | – | – | – | – | 0.62 | – |
| CHOL (±0.02) | – | – | – | – | – | – | – | – | – | – | – | – | – | – | 0.87 | 1.41 |
| LP encapsulation (% of the administered matter, (±3) | 100 | 99 | 98 | 96 | 94 | 98 | 99 | 96 | 96 | 93 | 93 | 94 | 94 | 92 | 97 | 94 |
| Size of the liposomes after preparation of the composition, nm (±3)/% of the liposomes having the corresponding size | 225/ 100 | 220/ 95 147/ 5 | 215/ 96 150/ 4 | 200/ 80 120/ 20 | 190/ 90 100/ 10 | 170/ 100 | 220/ 95 100/ 5 | 225/ 85 90/ 15 | 220/ 85 85/ 5 | 200/ 80 80/ 20 | 190/ 95 60/ 5 | 180/ 100 | 200/ 90 55/ 10 | 240/ 80 160/ 20 | 220/ 95 50/ 5 | 88/ 85 70/ 15 |
| Oxidation index, c.u. * | 0.22 | 0.21 | 0.20 | 0.24 | 0.25 | 0.26 | 0.27 | 0.26 | 0.25 | 0.26 | 0.26 | 0.27 | 0.27 | 0.27 | 0.28 | 0.28 |
| pH of the emulsion* | 7.1 | 7.1 | 7.0 | 7.1 | 7.1 | 7.0 | 7.0 | 7.0 | 7.0 | 7.0 | 5.5 | 7.1 | 7.0 | 7.0 | 7.1 | 5.5 |
| Residual solvents, %: * | | | | | | | | | | | | | | | | |
| ethyl alcohol | 0.02 | 0.02 | <0.02 | 0.03 | 0.03 | 0.02 | 0.02 | 0.02 | 0.02 | 0.01 | <0.02 | 0.02 | 0.02 | 0.04 | 0.02 | <0.06 |
| methyl alcohol | – | – | – | – | – | – | – | – | – | – | 0.01 | – | – | – | – | 0.01 |
| chloroform | 0.01 | 0.01 | <0.01 | 0.01 | 0.01 | 0.01 | 0.01 | 0.01 | 0.01 | 0.01 | 0.01 | 0.01 | 0.01 | <0.02 | 0.01 | <0.04 |
| acetonitrile | – | – | – | – | – | – | – | – | – | <0.01 | – | – | – | – | – | <0.02 |
| Osmolality, * mOsmol/kg | 320 | 300 | 310 | 300 | 310 | 310 | 320 | 300 | 300 | 280 | 280 | 310 | 320 | 330 | 300 | 280 |
| Sterility | + | + | + | + | + | + | + | + | + | + | + | + | + | + | + | + |

* is not regulated by the prototype

TABLE 4

The formulation of the liposomal composition of LP prepared by the claimed method and the prototype method in terms of the mass ratio of the components determined according to the established parameters of the pharmaceutical quality[1]

| Example No. | Mass ratio LP:ePC:DPPG:CHOL:lactose[2] |
|---|---|
| The composition prepared according to the claimed method | |
| 1 | 1:30.0:0.60:0.90:60.0 |
| 2 | 1:20.0:0.62:0.85:40.0 |
| 3 | 1:25.0:0.75:0.50:50.0 |
| 4 | 1:30.0:0.30:0.63:60 |
| 5 | 1:34.3:0.54:0.37:68.5 |
| 6 | 1:30.0:0.60:1.60:60.0 |
| 7 | 1:40.0:0.80:1.65:80.0 |
| 8 | 1:30.0:1.50:0.98:60.0 |
| 9 | 1:30.0:0.60:0.33:60.0 |
| 10 | 1:30.0:0.60:0.90:60.0 |
| 11 | 1:28.1:0.60:0.90:60.0 |
| 12 | 1:30.0:0.60:0.90:60.0 |
| 13 | 1:30.0:n/c (DPPG):0.90:60.0 |
| 14 | 1:29.4:0.60:0.80:60.0 |
| 15 | 1:29.1:0.60:0.87:60.0 |
| The composition prepared according to the prototype method | |
| 16 The prototype | 1(LP):10.60(ePC):n/c (DPPG):1.40 (CHOL):n/c (lactose) |

[1] The formulation of the compositions is stated after preparation of the frozen-dried product according to the Examples Nos. 1-14 and the liquid product according to the Example No. 15 according to the claimed method, as well as the liquid product according to the Example No. 16-prototype.
Water content in the products is not stated

[2] Lactose content is taken according to the administered quantity

[3] n/c means that the composition does not comprise the component

TABLE 5

The efficiency of the claimed method and of the prototype method in terms of the pharmacological activity of the prepared liposomal composition of LP for the daily drop administration in terms of influence onto the IOP level in case of ophthalmic hypertension

| Follow-up term, week | IOP level, mm Hg, (±0.60): | | | | | | |
|---|---|---|---|---|---|---|---|
| | Liposomal composition of LP[1] | | | | | | |
| | According to the claimed method (Example No.): | | | | | According to the prototype No. 16 | Analogue drug Lanotan[2] |
| | 1 | 2 | 3 | 13 | 15 | | |
| The initial IOP prior to the experiment = 11.90 ± 0.33 (intact control) | | | | | | | |
| The initial IOP in case of ophthalmic hypertension = 18.88 ± 0.73 (pathology control) | | | | | | | |
| 1 | 15.30 | 15.40 | 15.06 | 15.44 | 15.67 | 16.23 | 16.80 |
| 2 | 14.45 | 14.73 | 14.70 | 14.88 | 14.89 | 15.44 | 16.00 |
| 3 | 13.65 | 14.00 | 14.23 | 14.52 | 14.38 | 15.05 | 15.68 |
| 4 | 13.00 | 13.58 | 13.15 | 13.80 | 13.89 | 14.60 | 15.00 |
| 5 | 12.55 | 12.80 | 12.76 | 13.26 | 13.10 | 13.85 | 14.47 |
| 6 | 12.30 | 12.41 | 12.38 | 13.00 | 12.70 | 13.27 | 14.05 |
| 7 | 12.10 | 12.10 | 12.10 | 13.00 | 12.39 | 13.10 | 14.01 |
| 8 | 12.10 | 12.05 | 12.15 | 12.81 | 12.30 | 13.10 | 14.00 |
| 9 | 12.00 | 12.17 | 12.15 | 12.45 | 12.20 | 13.00 | 13.85 |
| 10 | 12.05 | 12.29 | 12.00 | 12.56 | 12.27 | 12.91 | 13.61 |
| 11 | 12.15 | 12.30 | 12.10 | 12.70 | 12.20 | 12.80 | 13.50 |
| 12 | 12.10 | 12.45 | 12.10 | 12.75 | 12.15 | 12.86 | 13.44 |

[1] data regarding the activity of the liposomal composition of LP according to the claimed method and to the prototype method are stated after their preparation and identification
[2] data regarding the activity of the analogue drug with actual expiration term is stated

TABLE 6

The efficiency of the claimed method and of the prototype method in terms of the pharmacological activity of the prepared liposomal composition of LP upon the single subconjunctival administration in terms of influence onto the IOP level in case of ophthalmic hypertension[1]

| Follow-up terms, weeks | The IOP level under action of the liposomal composition of LP, mm Hg (±0.66): | | | | | |
|---|---|---|---|---|---|---|
| | According to the claimed method (Example No.): | | | | | According to the prototype No. 16 |
| | 1 | 2 | 3 | 10 | 15 | |
| The initial IOP prior to the experiment = 12.40 ± 0.33 (intact control) | | | | | | |
| The initial IOP in case of ophthalmic hypertension = 19.39 ± 0.73 (pathology control) | | | | | | |
| 1 | 12.04 | 12.38 | 12.18 | 13.15 | 12.60 | 13.86 |
| 2 | 11.97 | 12.20 | 12.00 | 12.49 | 12.57 | 13.73 |
| 3 | 11.68 | 12.24 | 12.00 | 12.45 | 12.52 | 13.44 |
| 4 | 12.06 | 12.35 | 11.97 | 12.30 | 12.49 | 13.45 |
| 5 | 12.14 | 12.20 | 12.06 | 12.35 | 12.53 | 13.46 |
| 6 | 12.08 | 12.25 | 12.00 | 12.40 | 12.58 | 13.90 |
| 7 | 11.82 | 12.17 | 11.88 | 12.45 | 12.44 | 13.90 |
| 8 | 12.16 | 12.10 | 11.80 | 12.53 | 12.59 | 13.79 |
| 9 | 12.36 | 12.27 | 11.96 | 12.51 | 12.60 | 13.81 |
| 10 | 12.44 | 12.36 | 12.10 | 12.60 | 12.65 | 13.92 |
| 11 | 12.48 | 12.48 | 12.14 | 12.64 | 12.60 | 14.54 |
| 12 | 12.58 | 12.50 | 12.27 | 12.61 | 12.70 | 16.06 |

[1] data regarding the activity of the liposomal composition of LP according to the claimed method and to the prototype method are stated after preparation and identification

TABLE 7

The efficiency of the claimed method and of the prototype method in terms of the pharmacological activity of the prepared liposomal composition of LP upon the injection subconjunctival administration in terms of influence onto the IOP level in case of stable ophthalmic hypertension with glaucoma[1])

| Follow-up terms | OG (pathology-control) | According to the claimed method (Example No.): | | | | | According to the prototype No. 16 |
|---|---|---|---|---|---|---|---|
| | | 1 | 2 | 3 | 10 | 15 | |
| The initial IOP prior to the experiment = 16.44 ± 0.33 (intact control) | | | | | | | |
| 0 | 29.86 | 1st injection of the composition | | | | | |
| 3rd day | 30.06 | 18.69 | 18.53 | 18.27 | 19.20 | 19.03 | 24.44 |
| 1 week | 29.94 | 18.09 | 18.37 | 18.06 | 18.52 | 18.72 | 24.00 |
| 2 weeks | 29.25 | 18.19 | 18.40 | 17.93 | 18.44 | 18.40 | 24.10 |
| 4 weeks | 27.81 | 18.39 | 18.72 | 18.29 | 18.97 | 18.83 | 23.55 |
| 6 weeks | 28.28 | 18.87 | 19.10 | 18.90 | 19.43 | 19.24 | 24.21 |
| 2nd injection of the composition | | | | | | | |
| 7 weeks | 28.91 | 18.40 | 17.00 | 17.25 | 18.58 | 18.27 | 24.0 |
| 8 weeks | 27.90 | 17.74 | 17.46 | 17.63 | 18.70 | 17.97 | 24.20 |
| 10 weeks | 27.59 | 17.65 | 18.00 | 18.00 | 19.00 | 18.32 | 24.42 |
| 12 weeks | 27.44 | 17.73 | 18.16 | 18.10 | 19.43 | 18.48 | 24.00 |

[1])data regarding the activity of the liposomal composition of LP according to the claimed method and to the prototype method are stated after preparation and identification

TABLE 8

The efficiency of the claimed method and of the prototype method in terms of the pharmacological activity of the subconjunctival injections of the prepared liposomal composition of LP as to the influence onto the specific histomorphologic and biochemical parameters of the retina's condition in case of glaucoma with the stable OG*

| Specific parameters of the retina's condition | Prior to the experiment (intact control) | Glaucoma (pathology-control) | Influence of the liposomal composition of LP | | | | | The prototype No. 16 |
|---|---|---|---|---|---|---|---|---|
| | | | The claimed method (Example No.) | | | | | |
| | | | 1 | 2 | 3 | 10 | 15 | |
| Histomorphologic parameters | | | | | | | | |
| Neurons of the ganglionic layer: Density, c.u.: | | | | | | | | |
| magnification 100× | ≥20 | <10 | ≥18 | ≥19 | ≥20 | ≥16 | ≥18 | ≥9 |
| magnification 600× | ≥12 | ≤5-6 | ≥10 | ≥11 | ≥10 | ≥6 | ≥9 | ≥4 |
| Uniformity of the cell distribution | + | − | + | + | + | +/− | + | +/− |
| Presence of areas dropout | − | + | − | − | − | − | −/+ | +/− |
| Bipolar cells: | | | | | | | | |
| thinning of the layer width | − | + | − | − | − | −/+ | − | +/− |
| areas with the reduced number of neurons | − | + | − | −/+ | − | −/+ | −/+ | + |
| Biochemical parameters | | | | | | | | |
| Glutamate content, μmol/g | 13.3 ± 1.1 | 24.4 ± 1.9 | 13.7 ± 1.2 | 13.8 ± 1.3 | 14.2 ± 1.1 | 15.6 ± 1.2 | 14.0 ± 1.2 | 15.6 ± 1.7 |
| MDA content, nmol/g | 832.6 ± 56.8 | 1465.8 ± 84.6 | 877.4 ± 42.9 | 847.5 ± 46.2 | 896.5 ± 50.0 | 911.5 ± 40.7 | 900.3 ± 31.1 | 1074.3 ± 69.99 |

*the parameters were determined after the experiment ended according to the scheme stated in the Table 7.

TABLE 9

The stability of the liposomal composition of LP prepared by the claimed method and by the prototype method in terms of the parameters of the pharmaceutical and pharmacological quality

| | Value of the quality parameter of the liposomal composition of LP | | | | | | | | | | | | |
|---|---|---|---|---|---|---|---|---|---|---|---|---|---|
| | Example No. according to the claimed method: | | | | | | | | | | | No. 16- Prototype | |
| | 1 | | | 3 | | | 13 | | | 15 | | | |
| | Storage term (month) at a temperature of (±0.5° C.): | | | | | | | | | | | | |
| | −20° C. | | | | | | | | | 4° C. | | 4° C. | |
| Parameters | 0 | 6 | 12 | 0 | 6 | 12 | 0 | 6 | 12 | 0 | 6 | 0 | 6 |
| Pharmaceutical quality | | | | | | | | | | | | | |
| Content of the identified components * | | | | | | | | | | | | | |
| LP (±0.02) | 0.50 | 0.50 | 0.50 | 0.52 | 0.49 | 0.49 | 0.51 | 0.50 | 0.49 | 1.03 | 0.97 | 1.01 | 0.90 |
| ePC (±0.15) | 15.0 | 15.0 | 14.8 | 13.0 | 13.1 | 12.9 | 15.2 | 15.0 | 14.8 | 29.93 | 27.25 | 10.70 | 8.40 |
| DPPG (±0.02) | 0.30 | 0.29 | 0.29 | 0.39 | 0.36 | 0.37 | n/c | n/c | n/c | 0.62 | 0.48 | n/c | n/c |
| CHOL (±0.02) | 0.45 | 0.45 | 0.43 | 0.30 | 0.30 | 0.29 | 0.46 | 0.47 | 0.45 | 0.87 | 0.64 | 1.41 | 1.01 |
| Non-identified impurities (±0.03) * | <0.02 | <0.02 | <0.03 | <0.02 | <0.02 | <0.04 | <0.02 | <0.04 | <0.04 | <0.02 | 0.08 | <0.02 | 0.10 |
| LP encapsulation (% of the overall content, (±5) | 100 | 99 | 97 | 99 | 98 | 96 | 94 | 92 | 92 | 98 | 86 | 94 | 72 |
| Size of the liposomes, (nm (±3)/% of the liposomes having the corresponding size) | 225/ 100 | 223/ 100 | 220/ 95 110/ 5 | 220/ 95 147/ 5 | 220/ 94 127/ 6 | 218/ 95 124/ 5 | 210/ 93 65/ 7 | 210/ 88 65/ 7 | 210/ 88 55/ 12 56/ 5 | 220/ 95 50/ 5 | 200/ 78 55/ 22 | 88/ 85 70/ 15 | 94/ 20 88/ 50 50/ 30 |
| Oxidation index, c.u. | 0.23 | 0.24 | 0.25 | 0.22 | 0.26 | 0.26 | 0.30 | 0.31 | 0.32 | 0.28 | 0.33 | 0.29 | 0.40 |
| pH of the emulsion | 7.1 | 7.1 | 7.1 | 7.0 | 7.0 | 6.9 | 7.1 | 7.0 | 7.0 | 7.0 | 6.7 | 5.5 | 5.5 |
| Osmolality, mOsmol/kg | 320 | 315 | 310 | 310 | 300 | 300 | 320 | 310 | 300 | 300 | 250 | 280 | 250 |
| Sterility | + | + | + | + | + | + | + | + | + | + | +/− | + | +/− |
| Pharmacological quality | | | | | | | | | | | | | |
| Effect of the single s/c injection as to the IOP level in case of OG, % up to the initial IOP (intact)/up to the IOP (pathology-control) (±5.3%): | | | | | | | | | | | | | |
| in 1 week | 97.1/ 67.8/ | 99.7/ 63.8 | 100.4/ 64.2 | 98.2/ 62.8 | 100.1/ 64.0 | 100.5/ 64.3 | 106.9/ 68.3 | 106.5/ 68.1 | 107.3/ 68.6 | 101.6 65.0 | 116.1/ 74.2 | 111.8/ 71.5 | 135.2/ 86.5 |
| in 2 weeks | 96.5/ 61.7 | 96.8/ 61.9 | 98.4/ 62.9 | 96.8/ 61.9 | 100.0/ 64.0 | 100.9/ 64.5 | 104.8 67.0 | 106.9/ 68.3 | 107.7/ 68.8 | 101.4/ 64.8 | 121.0/ 77.3 | 111.7/ 71.3 | 140.6/ 89.9 |
| in 6 weeks | 97.4/ 62.3 | 98.9/ 63.2 | 99.2/ 61.9 | 96.8/ 61.9 | 100.7/ 64.4 | 101.6/ 65.0 | 104.0/ 66.5 | 108.1/ 69.1 | 108.7/ 69.5 | 101.0/ 64.6 | 128.7/ 82.0 | 112.1/ 71.7 | 145.2/ 92.8 |
| Effect as to the glutamate level in the retina in 6 weeks after the single s/c injection, % up to the initial values (intact)/up to the values in the pathology-control (±4.5%) | 103.0/ 56.1 | 106.0/ 57.8 | 107.2/ 58.2 | 102.3/ 55.7 | 103.8/ 56.6 | 104.5/ 57.0 | 106.7/ 58.2 | 108.3/ 59.0 | 107.5/ 58.6 | 105.3/ 57.4 | 127.6/ 69.7 | 117.3/ 63.9 | 136.8/ 74.6 |
| Effect as to the MDA level in the retina in 6 weeks after the single s/c injection, % up to the initial values (intact)/ up to the values in the pathology-control (±3.7%) | 105.4/ 59.9 | 106.9/ 60.8 | 107.5/ 61.1 | 104.3/ 59.3 | 104.7/ 59.5 | 105.3/ 59.8 | 107.1/ 60.9 | 107.6/ 61.1 | 109.1/ 62.0 | 108.1/ 61.4 | 132.0/ 76.3 | 141.7/ 80.5 | 160.9/ 91.4 |

* The quantitative content is stated in mg/bottle for the composition according to the Examples Nos. 1, 3, 13 and mg/ml for the Examples Nos. 15 and 16-prototype.

TABLE 10

The stability of the formulation of the liposomal composition of LP prepared by the claimed method and by the prototype method in terms of the mass ratio of the components

| Liposomal composition of LP (Example No.) in the selected conditions | Mass ratio * LP:ePC:DPPG:CHOL:lactose |
|---|---|
| The composition prepared according to the claimed method | |
| No. 1 - Storage at −20° C. during (month): | |
| 0 months (ex tempora) | 1:30.0:0.60:0.90:60.0 |
| 6 months | 1:30.0:0.58:0.90:60.0 |
| 12 months | 1:29.6:0.58:0.87:60.0 |
| No. 3 - Storage at −20° C. during (month): | |
| 0 months (ex tempora) | 1:25.0:0.75:0.50:50.0 |
| 6 months | 1:25.0:0.73:0.58:50.0 |
| 12 months | 1:25.0:0.75:0.50:50.0 |
| No. 13 - Storage at −20° C. during (month): | |
| 0 months (ex tempora) | 1:30.0:n/c (DPPG):0.90:60.0 |
| 6 months | 1:30.0:n/c (DPPG):0.94:60.0 |
| 12 months | 1:30.2:n/c (DPPG):0.91:60.0 |
| No. 15 - Storage at 4° C. during (month) | |
| 0 months (ex tempora) | 1:29.1:0.60:0.87:60.0 |
| 6 months | 1:28.1:0.49:0.77:60.0 |
| The composition prepared according to the prototype method | |
| No. 16 - Storage at 4° C. during (month): | |
| 0 months (ex tempora) | 1:10.60:n/c (DPPG):1.40:n/c (lactose) |
| 6 months | 1:9.30:n/c (DPPG):1.04:n/c (lactose) |

* Mass ratio of the components is calculated according to the determined content of LP, ePC, DPPG, and CHOL (parameters of the pharmaceutical quality) at a certain storage term of the product. Lactose content is taken according to the administered quantity.

LITERATURE

1. Resnikoff S., Pascolini D., Etyale I. et al. Global data on visual inpairment//Bull.World Health Organ.—2004.—v. 82, N 11. p 0.844-851.
2. Quigley H. A., Broman A. T. The number of people with glaucoma worldwide in 2010 and 2020//Br. J.Ophtalmol.—2006, v. 90, N 3, p. 262-267.
3. Zavgorodnaya N. G., Pasechnikova N. V. Primary glaucoma. New vision of the old problem//Zaporozhye: Orbita-YUG.—2010.—192 p.
4. Hoyng P., van Beek L. Pharmacological therapy for glaucoma: a review//Drugs.—2000, v.59, N 3, p. 411-434.
5. Andres-Guerro V., Vicario-de la Torre M., Molina-Martines I. Comparison of tolerance and efficiency of traditional tymolol maleate eye drops versus new bioadgesive formulation//Invest. Ophtalm. Vis.Sci.—2011, v.52, p. 3548-3556.
6. Latanoprost.—Nation. Library of Med., Nation. Centre of Biotech. 2020-08-29.
7. Alm A., Stjernschanctz J. Effects on intraocular pressure and side effect of latanoprost applied once daily//Ophtalmology.—1995.—v.102, N 12, p. 1743-1752.
8. Progress in drug and vaccine delivery: Abst. of annual conferences Liposome advances. —London-Athen, 1990-2018.
9. Ako-AdounvoA., Nagarval R., Oliveira L. Recent patent formulation and therapeutical implication.—Recent Pat. Drug Deliv. Formul. 2014, 8(3), p. 193-191.
10. Cheng Y., Hung K., Tsaietal T. Sustained delivery of latanoprost by thermosensitive chitosan-gelatin-hydrogel for controlling ocular hypertension.—Acta Biomaterials, 2014, v.10, N 10, p. 4360-4366.
11. FathallaD., Fouad E., Soliman G. Latanoprost niosomes as a sustained realease ocular delivery for the management of glaucoma.—Drug Develop. and Indust. Pharmacy. 2020, v.46, N 5, p. 806-813.
12. Grygoryeva G. S., Krasnopolsky Yu.M. Liposomes per se: pharmacotherapeutic status. —Pharmacology and medical toxicology.—2020, V.14.—No 4, p. 264-271
13. FDA, 2014: Recent requirements for innovated liposomal drugs and liposomal nanosimilars; State pharmacopeia of Ukraine, 2015: Liposomal drugs N.
14. WO 2012/021107 A2, Int. Publ. Date 16 Feb. 2012. Venkatraman S., Chattopadhyay S., Natarajan J. V. et al. A liposomal formulation for ocular drug delivery.
15. US 2013/0216606 A1, Pub.Date 22 Aug. 2013. Venkatraman S., Natarajan J. V., Wong T., Yin Chaiang F. B. Liposomal formulation for ocular drug delivery.
16. SG 187770 (A1), Pub. Date 28 Mar. 2013. A liposomal formulation for ocular drug delivery.
17. Natarajan J. V., Darvitan A., Barathi V. A. et al. Sustained drug release in nanomedicine: a long-acting nano-carrier formulation for glaucoma. ACS Nano, 2014, 8, No 1, p. 419-429, doi 10.1022/nn4046024.
18. T. T. Wong, G. D. Novack, J. V. Natarajanet et al. Nanomedicine for glaucoma: sustained release latanoprost offer a new therapeutic option with substantial benefits over eye drops. Drug Deliv. and Transl. Res. 2014, doi 10.1007/s13346-014-0196-9.
19. Natarajan J. V., Ang M., Darvitan A. et al. Nanomedicine for glaucoma: liposomes provide sustained release latanoprost in the eye.—Int. J. Nanomedicine, 2012, N 7, p. 123-131, doi 10.2147/IJN.S25468.
20. Natarajan J. V., Chattopadhyay S.,Ang M. et al. Sustained release of anti-glaucoma drug: Demonstration of efficacy of a liposomal formulation on rabbit eye.—2011//doi.org/10.1371/journal pone 0024513.
21. Franze S., Selmin F., Samaritani E. et al. Liophilization of liposomal formulation, still necessary, still challenging.—Pharmaceutics, v.10, N 3, p. 139-170.
22. Gregoriadis G. (ed.). Liposome technology.—vol. 3: Informa Healthcare, USA, N-Y.—2007, p. 79-94.
23. Clin. Trials. gov. NCT 01987323.—Safety and effects of liposomal latanoprost in ocular hypertension.—US National Library of Medicine, 2013.
24. European Convention on protection of spinal animals used for research or other scientific purposes dated 18 Mar. 1986: Verkhovna Rada of Ukraine, official webportal: International documents (Council of Europe).
25. Kim H. G. Experimental chronic ocular hypertension by anterior chamber injection of 0.3% carbomer solution in the rat/H. G. Kim, J. W. Park//Clin. Exp. Ophthalmol.—2013.—V. 41.—P. 404-412.
26. Wang Y. Y. Experimental study of carbomer glaucoma model in rabbits by injecting different location in anterior chamber/Y. Y. Wang//Ophthalmol.—2009.—V. 45.—P. 91-95.
27. Yegorov Ye. A. Neuroprotection in case of glaucoma: modern opportunities and perspectives/A. Yu. Brezhnev, A. Ye. Yegorov//Clinical opthalmology.—2014.—V. 14, No 2.—P. 108-112.

28. Yoles E. Elevation of intraocular glutamate levels in rats with partial lesion of the optic nerve/E. Yoles, M. Schwartz//Arch.Ophthalmol.—1998.—V. 116.—P. 906-910.
29. Experimental studies of harmlessness and pharmacological activity of ophthalmologic drugs. Methodical recommendations SPC MOH of Ukraine//Kyiv, 2003.—43 p.
30. National guidance as to glaucoma/Ed. by prof. Ye. A. Yegorov, prof. Yu. S. Astakhov, prof. A. G. Schuko.—2nd Ed., con. and suppl.—M.: GEOTAR-Media, 2011.—280 p.

The invention claimed is:

1. A method for preparing a liposomal composition comprising:
    creating a mixture of solutions of latanoprost, egg phosphatidylcholine, and cholesterol in organic solvents, by combining:
    latanoprost, egg phosphatidylcholine, and cholesterol that are provided in ethyl alcohol; and
    dipalmytoyl phosphatidylglycerol provided in a mixture of ethyl alcohol and chloroform to form the mixture of solutions;
    vacuum drying the mixture of solutions;
    emulsifying the dried mixture of solutions in an aqueous lactose solution in a pH 7.1 buffer to form an emulsion;
    dispersing the emulsion at a stepwise pressure increase from 300 to 800 at;
    performing a sterilizing filtration; and
    freeze drying to form a freeze-dried liposomal composition under compliance of the following mass ratios:
    egg phosphatidylcholine:lactose being 1:2;
    egg phosphatidylcholine:dipalmytoyl phosphatidylglycerol:latanoprost being 1:0.02-0.04:0.03-0.05; and
    egg phosphatidylcholine, dipalmytoyl phosphatidylglycerol, and latanoprost:cholesterol being 1:0.02-0.04.

2. A pharmacologically active liposomal composition for ophthalmotherapy prepared by the method of claim 1, the composition comprising latanoprost, egg phosphatidylcholine, cholesterol, dipalmytoyl phosphatidylglycerol, and lactose, wherein the composition is a freeze-dried powder having the following mass ratio:
    Latanoprost 1,
    Egg phosphatidylcholine 20.0-30.0,
    Dipalmytoyl phosphatidylglycerol 0.6-0.75,
    Cholesterol 0.5-0.9,
    Lactose 40.0-60.0,
    Water residue the remainder.

3. The composition according to claim 2, wherein the composition has an antihypertensive and neuroprotective action in case of ocular hypertension and glaucoma.

4. The composition according to claim 2, wherein the composition is suitable for preparation of a solution for an instillation use and/or an injectable subconjunctival administration.

* * * * *